US012773323B1

(12) United States Patent
White et al.

(10) Patent No.: US 12,773,323 B1
(45) Date of Patent: Oct. 27, 2026

(54) SYSTEMS AND METHODS FOR AN EXPANDABLE ANTERIOR LUMBAR INTERBODY FUSION DEVICE

(71) Applicant: Dignity Health, San Francisco, CA (US)

(72) Inventors: Michael White, San Francisco, CA (US); Juan Uribe, San Francisco, CA (US); Dakota Graham, San Francisco, CA (US); Phillip Warren, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 19/190,396

(22) Filed: Apr. 25, 2025

Related U.S. Application Data

(60) Provisional application No. 63/638,814, filed on Apr. 25, 2024.

(51) Int. Cl.

| | |
|---|---|
| ***A61F 2/44*** | (2006.01) |
| ***A61B 17/70*** | (2006.01) |
| ***A61F 2/46*** | (2006.01) |
| *A61F 2/30* | (2006.01) |

(52) U.S. Cl.
CPC ........ *A61F 2/4455* (2013.01); *A61B 17/7032* (2013.01); *A61F 2/4611* (2013.01); *A61F 2002/30538* (2013.01); *A61F 2002/30556* (2013.01)

(58) Field of Classification Search
CPC ...... A61F 2/4455; A61F 2/446; A61F 2/4465; A61F 2/447; A61F 2002/30537; A61F 2002/30555; A61F 2002/30556; A61F 2002/30266; A61F 2002/30281; A61F 2002/30538
See application file for complete search history.

(56) References Cited

U.S. PATENT DOCUMENTS

| | | | | |
|---|---|---|---|---|
| 2008/0051890 | A1* | 2/2008 | Waugh | A61F 2/442 623/17.11 |
| 2018/0147066 | A1* | 5/2018 | Daffinson | A61F 2/447 |
| 2021/0121299 | A1* | 4/2021 | Hyder | A61F 2/4455 |
| 2021/0378832 | A1* | 12/2021 | Altarac | A61F 2/447 |
| 2022/0183854 | A1* | 6/2022 | Altarac | A61F 2/4611 |

* cited by examiner

*Primary Examiner* — Jan Christopher L Merene
(74) *Attorney, Agent, or Firm* — Polsinelli PC

(57) ABSTRACT

An adjustable intervertebral fusion device includes a compact arrangement of a coronal adjustment mechanism and a sagittal adjustment mechanism that enables fine-tuning and adjustments in both lumbar lordosis and coronal angle following placement within an intervertebral space. The coronal adjustment mechanism includes a coronal advancer in operative association with a coronal lifter that collectively control a coronal angle adjustment provided by the device while maintaining a compact starting height. The sagittal adjustment mechanism includes a sagittal advancer in operative that collectively controls a sagittal angle adjustment provided by the device.

18 Claims, 24 Drawing Sheets

ANTERIOR VIEW

LATERAL VIEW

LATERAL VIEW

LATERAL VIEW

SYSTEMS AND METHODS FOR AN EXPANDABLE ANTERIOR LUMBAR INTERBODY FUSION DEVICE

CROSS-REFERENCE TO RELATED APPLICATIONS

This is a U.S. Non-Provisional Patent Application that claims benefit to U.S. Provisional Patent Application Ser. No. 63/638,814 filed Apr. 25, 2024, which is herein incorporated by reference in its entirety.

FIELD

The present disclosure generally relates to surgical implants, and in particular, to an expandable anterior lumbar interbody fusion device that is operable for independent expansion in a coronal plane and a sagittal plane.

BACKGROUND

Interbody fusion devices, or "cages" are used in surgical applications to promote fusion and can also aid in the correction of spinal deformity. For example, individuals with scoliosis will have deformity in both the coronal and sagittal planes requiring correction, and interbody cages are often used to help restore the normal alignment of the spine.

It is with these observations in mind, among others, that various aspects of the present disclosure were conceived and developed.

BRIEF DESCRIPTION OF THE DRAWINGS

FIG. 2A shows an anterior view, FIG. 2B shows a lateral view, FIG. 2C shows a lateral view demonstrating adjustment of a coronal adjustment mechanism of the expandable ALIF device, and FIG. 2D shows a lateral view demonstrating adjustment of a sagittal adjustment mechanism of the expandable ALIF device.

FIG. 8A shows a top perspective view of the coronal advancer and FIG. 8B shows a bottom perspective view of the coronal advancer.

FIG. 9A shows a top (anterior) perspective view of the coronal lifter, FIG. 9B shows a bottom (anterior) perspective view of the coronal lifter, FIG. 9C shows a bottom (posterior) perspective view of the coronal lifter, and FIG. 9D shows a cutaway perspective view of the coronal lifter;

FIG. 10A shows a first configuration, FIG. 10B shows a second configuration with the coronal advancer raising the coronal lifter, and FIG. 10C shows a cutaway view demonstrating a dovetail engagement between the coronal advancer and the coronal lifter.

FIG. 12A shows a top perspective view of the sagittal advancer and FIG. 12B shows a below perspective view of the sagittal advancer coupled along a sagittal advancer track of a center body of the expandable ALIF device.

FIG. 13A shows a perspective view of the applicator device coupled with the ALIF device, FIG. 13B shows a perspective view of the applicator device including a gearbox for adjustment of the expandable ALIF device, and FIG. 13C shows a top plan view demonstrating operation of the gearbox for adjustment of the expandable ALIF device.

Corresponding reference characters indicate corresponding elements among the view of the drawings. The headings used in the figures do not limit the scope of the claims.

DETAILED DESCRIPTION

The present disclosure outlines an expandable anterior lumbar interbody fusion (ALIF) device that enables lordotic and coronal plane adjustment after insertion and minimizes a starting height of the device in order to ease insertion. The ALIF device includes a vertically-compact coronal adjustment mechanism and sagittal adjustment mechanism that enable independent adjustment of the ALIF device in multiple directions following insertion.

In some examples, the ALIF cage can be positioned between vertebrae ranging from L4 of the lumbar spine to S1 of the sacral curve.

1. Introduction

Figure 1B:
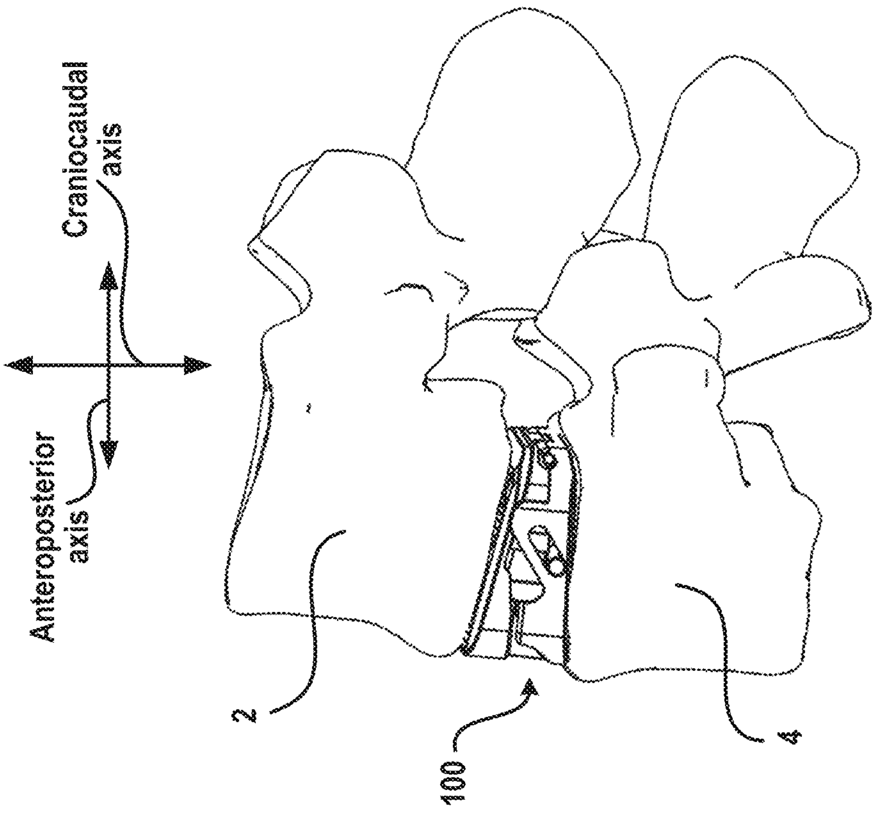
FIGS. 1A and 1B are a pair of illustrations respectively showing a perspective view and a lateral view of an expandable anterior lumbar interbody fusion (ALIF) device positioned between two vertebrae.
Figure 1A:
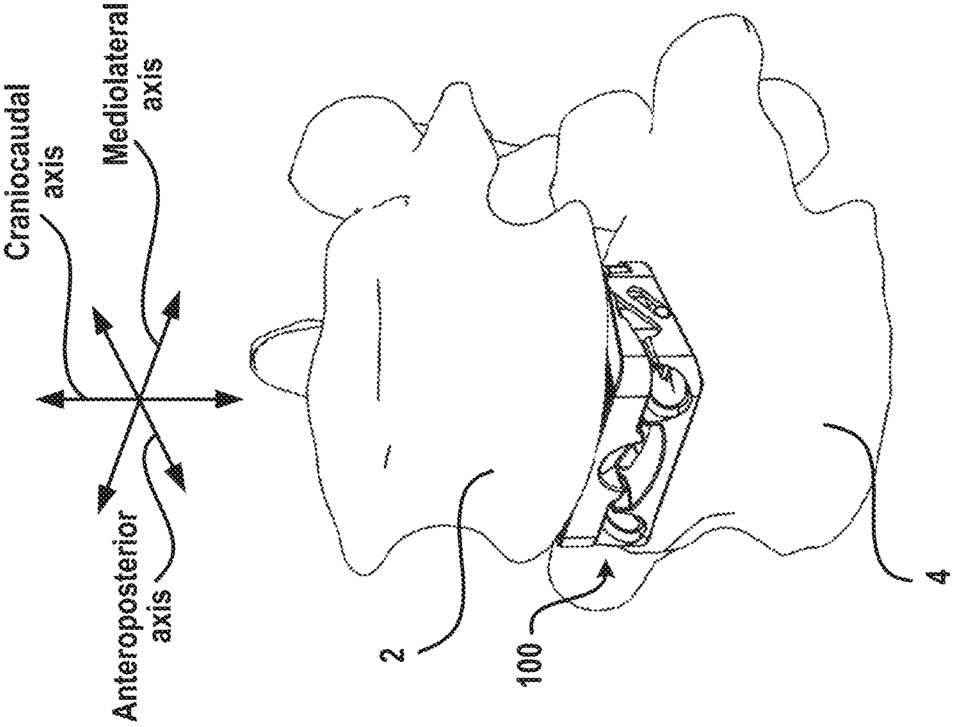

FIGS. 1A and 1B show an ALIF device 100 for selective and independent expansion of an intervertebral space, i.e., between a first vertebra 2 and a second vertebra 4 of a vertebral structure. Most interbody fusion devices are static and do not allow for fine-tuning and adjustments in both lumbar lordosis and the coronal angle of the cage, particularly after placement in the disc space. Further, a compact minimum height is necessary to enable insertion into the intravertebral space. As such, the ALIF device 100 outlined herein includes a compact arrangement of a coronal adjustment mechanism and a sagittal adjustment mechanism that enables fine-tuning and adjustments in both lumbar lordosis and coronal angle. FIGS. 1A and 1B also relate spatial terms “craniocaudal axis”, “anteroposterior axis”, and “mediolateral axis” to an orientation of the ALIF device 100, the first vertebra 2, and the second vertebra 4.

Figures 2A, 2B, 2C, 2D:
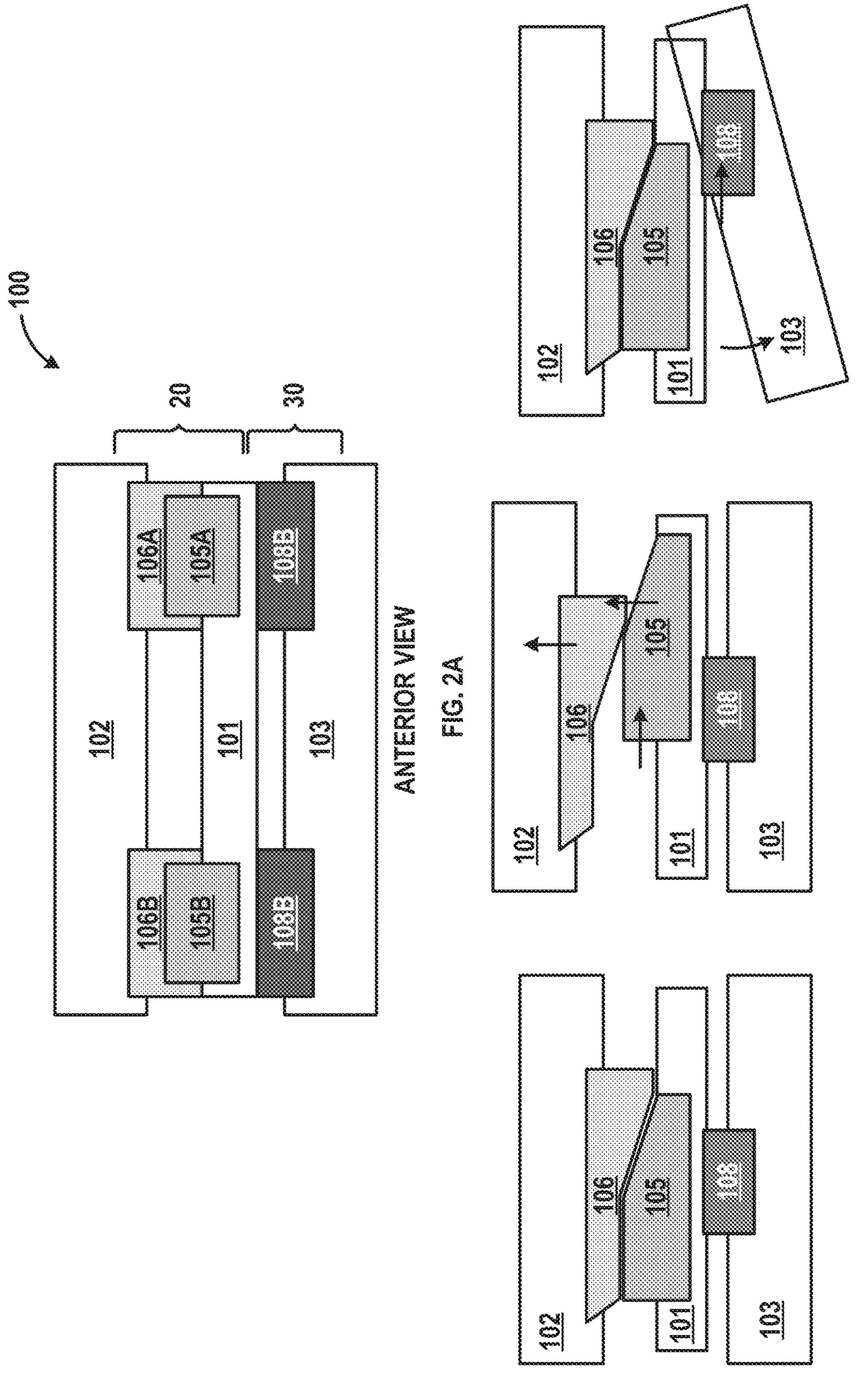
FIGS. 2A-2D are a series of simplified illustrations showing an expandable ALIF device, where

FIGS. 2A-2D show simplified diagrams of the ALIF device 100. In particular, FIG. 2A shows a front (anterior) view of the ALIF device 100 including a center body 101, which provides a central support structure for various moving components of the ALIF device 100. The ALIF device 100 further includes a first plate 102 and a second plate 103 which collectively encapsulate the center body 101, as well as a coronal adjustment mechanism 20 and a sagittal adjustment mechanism 30 outlined further herein. The first plate 102 is positioned above the center body 101 and, when the ALIF device 100 is positioned between vertebra as in FIGS. 1A and 1B, engages an underside of the first vertebra 2. Likewise, the second plate 103 is positioned below the center body 101 and engages a top side of the second vertebra 4.

In the example, the coronal adjustment mechanism 20 is generally localized between the center body 101 and the first plate 102, and serves to adjust coronal expansion of the ALIF device 100. Further, the sagittal adjustment mechanism 30 is generally localized between the center body 101 and the second plate 103, and serves to adjust sagittal expansion of the ALIF device 100.

FIGS. 2B and 2C show simplified side views of the ALIF device 100 of FIG. 2A. As shown, the coronal adjustment mechanism 20 includes two coronal advancers 105 (e.g., a first coronal advancer 105A associated with a first lateral side of the ALIF device 100 and a second coronal advancer 105B associated with a second lateral side of the ALIF device 100), where each coronal advancer 105 is positioned along a top portion of the center body 101. Each coronal advancer 105 respectively engages a coronal lifter 106 (e.g., a first coronal lifter 106A engaging the first coronal advancer 105A and a second coronal lifter 106B engaging the second coronal advancer 105B), where each coronal lifter 106 is positioned along a bottom portion of the first plate 102. The coronal advancers 105 are each movable along the center body 101 (along the anteroposterior axis) relative to their respective coronal lifter 106 by a coronal advancer screw to adjust a height of the first plate 102 relative to the center body 101. As illustrated between FIGS. 2B and 2C, this is accomplished by moving the coronal advancer 105 along an anteroposterior axis (in the transverse plane) along the center body 101, thereby actuating the coronal lifter 106 along the craniocaudal axis, which in turn actuates the associated lateral side of the first plate 102 along the craniocaudal axis relative to the center body 101.

FIG. 2D shows a simplified side view of the ALIF device 100 of FIG. 2A following sagittal adjustment (e.g., lumbar lordosis). As shown, the sagittal adjustment mechanism 30 includes two sagittal advancers 108 (e.g., a first sagittal advancer 108A associated with a first lateral side of the ALIF device 100 and a second sagittal advancer 108B associated with a second lateral side of the ALIF device 100), where each sagittal advancer 108 is positioned along a bottom portion of the center body 101 and a top portion of the second plate 103. Similar to the coronal advancers 105, the sagittal advancers 108 are each movable along the center body 101 (along the anteroposterior axis) by a sagittal advancer screw to adjust sagittal expansion of the first plate 102 relative to the center body 101. As illustrated between FIGS. 2B and 2D, moving the sagittal advancer 108 along the anteroposterior axis (in the transverse plane) along the center body 101 rotates the second plate 103 relative to the center body 101 (about an axis that is parallel to the mediolateral axis).

Figure 3A:
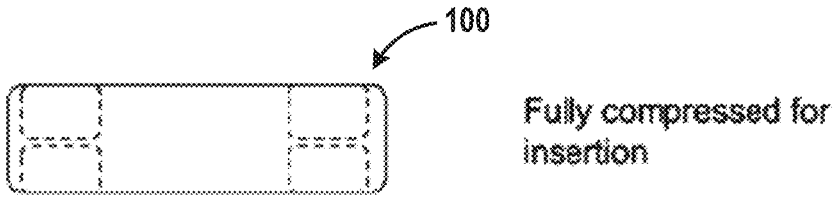
FIGS. 3A-3E are simplified illustrations showing various example configurations of an expandable ALIF device from an anterior view.
Figure 3B:
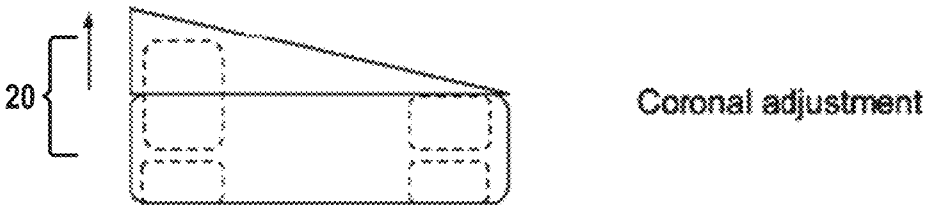
Figure 3C:
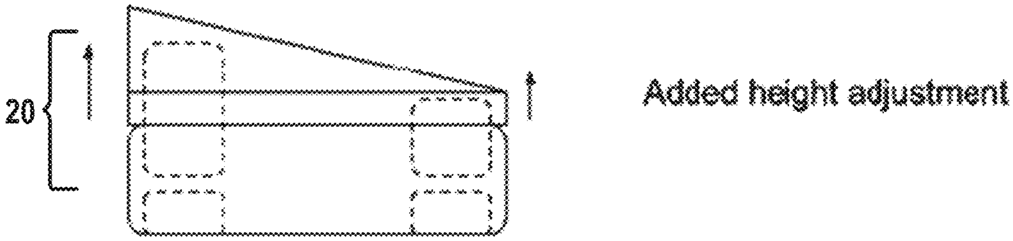
Figure 3D:
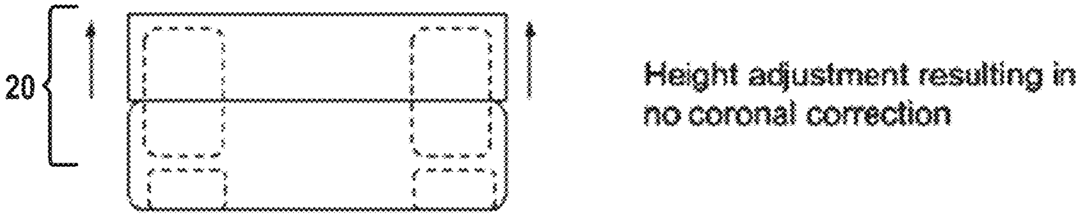
Figure 3E:
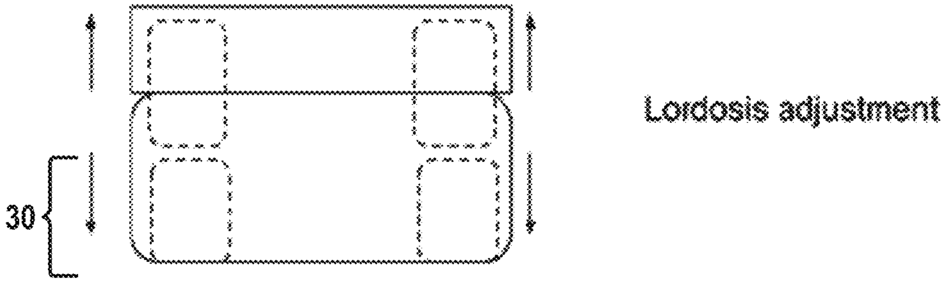

FIGS. 3A-3E are a series of simplified front views showing coronal and sagittal adjustment of the ALIF device 100. FIG. 3A shows a “fully compressed” configuration of the ALIF device 100. FIG. 3B shows coronal adjustment of one lateral side of the ALIF device 100 (e.g., a left side from the perspective of the viewer) using only one side of the coronal adjustment mechanism 20. FIG. 3C shows an added height adjustment to both lateral sides of the ALIF device 100 using both sides of the coronal adjustment mechanism 20. FIG. 3D shows equal height adjustment to both lateral sides of the ALIF device 100 using both sides of the coronal adjustment mechanism 20, which would result in no “coronal” correction but would result in expansion of an intravertebral space along a craniocaudal axis. Finally, FIG. 3E shows lordosis adjustment of both lateral sides of the ALIF device 100 using both sides of the sagittal adjustment mechanism 30 (the effect of which is demonstrated in the lateral view of FIG. 2D).

Figure 4A:
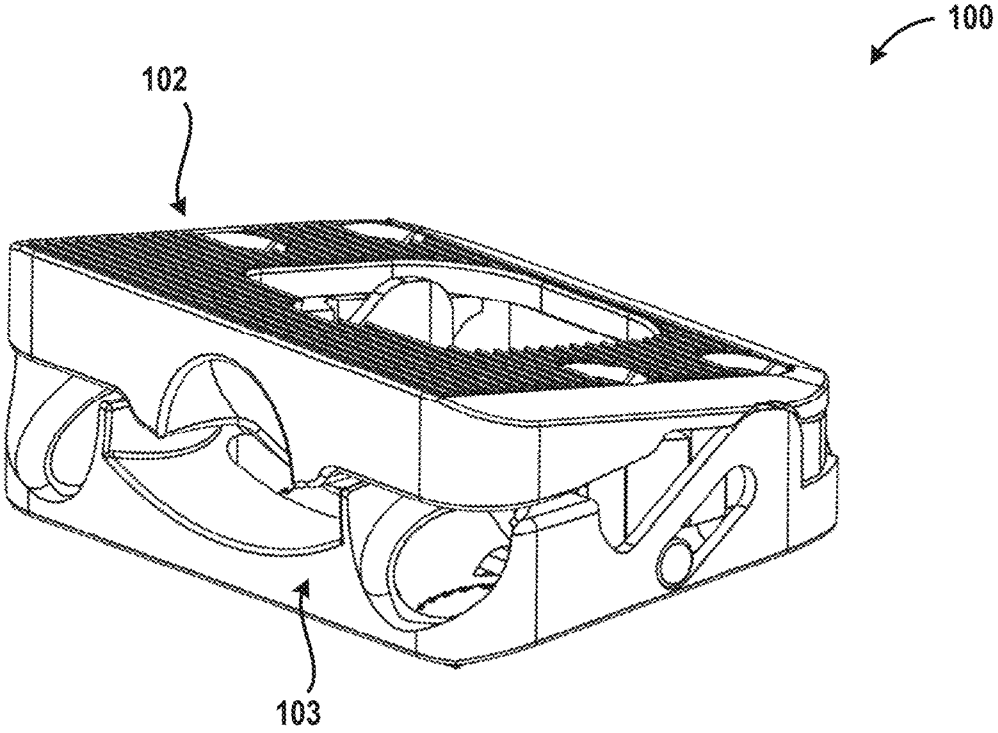
FIG. 4A is a detailed illustration showing an anterior perspective view of an expandable ALIF device.
Figure 4B:
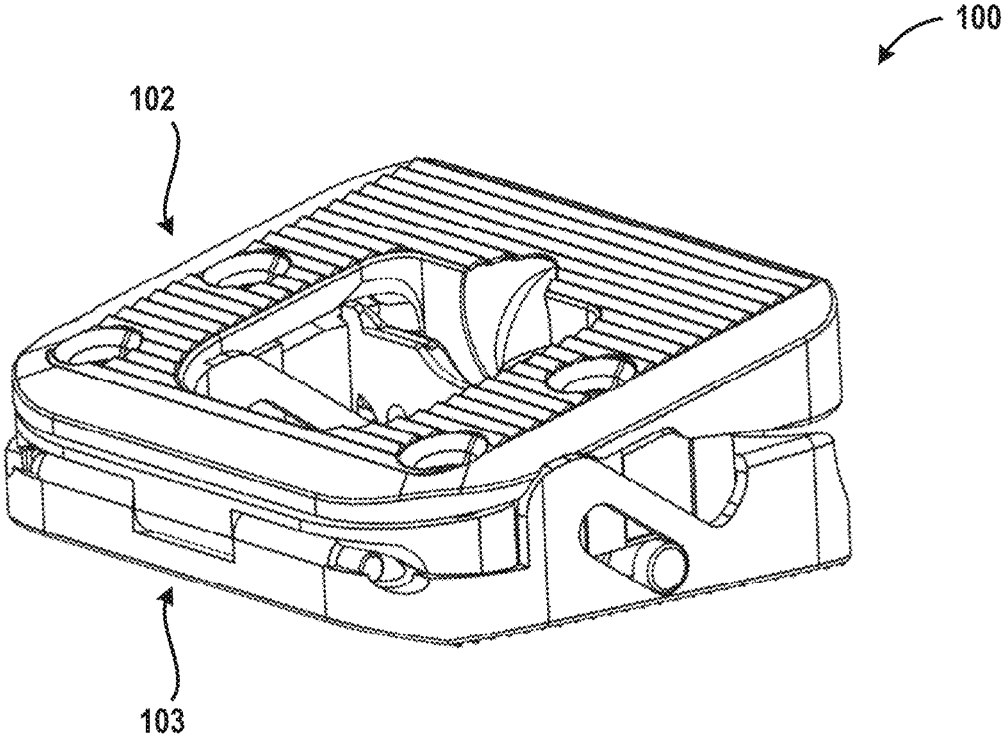
FIG. 4B is a detailed illustration showing a posterior perspective view of an expandable ALIF device.
Figure 4C:
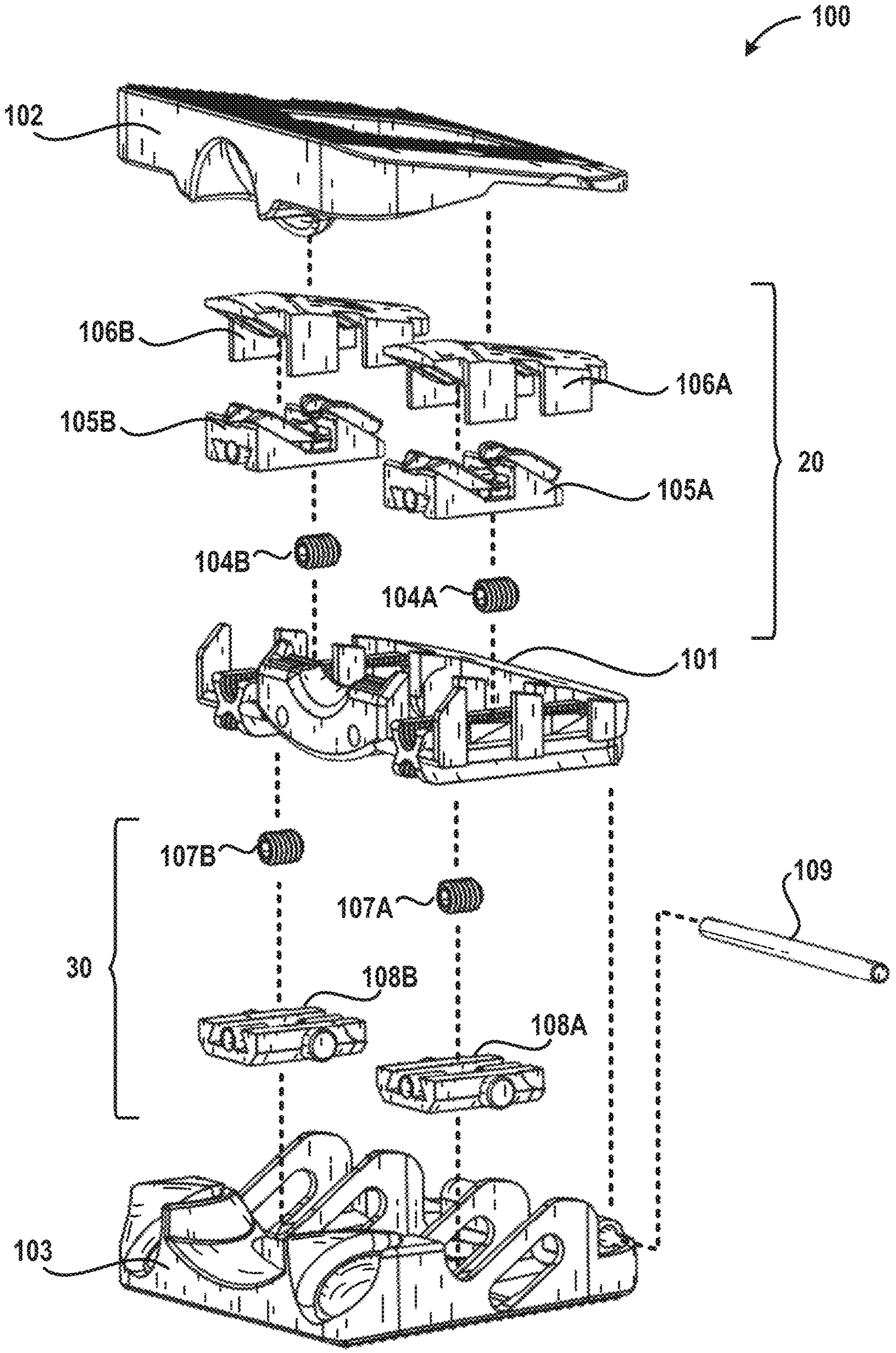
FIG. 4C is a detailed illustration showing an exploded view of an expandable ALIF device.

FIGS. 4A-4C show detailed illustrations of the ALIF device 100, where FIG. 4A shows an anterior perspective view and FIG. 4B shows a posterior perspective view of the ALIF device 100 featuring the first plate 102 and the second plate 103. FIG. 4C shows an exploded view of the ALIF device 100 of FIG. 4A. As shown, the ALIF device 100 can include the coronal adjustment mechanism 20 and the sagittal adjustment mechanism 30. In the example, the coronal adjustment mechanism 20 is generally localized between the center body 101 and the first plate 102, and serves to adjust coronal expansion of the ALIF device 100. Further, the sagittal adjustment mechanism 30 is generally localized between the center body 101 and the second plate 103, and serves to adjust sagittal expansion of the ALIF device 100.

As shown in FIG. 4C, the coronal adjustment mechanism 20 includes the coronal advancers 105 (e.g., the first coronal advancer 105A associated with a first lateral side of the ALIF device 100 and the second coronal advancer 105B associated with a second lateral side of the ALIF device 100), where each coronal advancer 105 is positioned along a top portion of the center body 101. The coronal advancers 105 engage the coronal lifters 106 (e.g., the first coronal lifter 106A engaging the first coronal advancer 105A and the second coronal lifter 106B engaging the second coronal advancer 105B), where each coronal lifter 106 is positioned along a bottom portion of the first plate 102. The coronal advancers 105 are each movable along the center body 101 relative to their respective coronal lifter 106 by a coronal advancer screw (a first coronal advancer screw 104A for moving the first coronal advancer 105A and a second coronal advancer screw 104B for moving the second coronal advancer 105B) to adjust coronal expansion of the first plate 102 relative to the center body 101, as discussed and illustrated in further detail herein (see sections 1.1 and 2.3).

As further shown in FIG. 4C, the sagittal adjustment mechanism 30 includes the sagittal advancers 108 (e.g., the first sagittal advancer 108A associated with a first lateral side of the ALIF device 100 and the second sagittal advancer 108B associated with a second lateral side of the ALIF device 100), where each sagittal advancer 108 is positioned along a bottom portion of the center body 101 and engages the second plate 103. The sagittal advancers 108 are each movable along the center body 101 by a sagittal advancer screw (first sagittal advancer screw 107A and second sagittal advancer screw 107B) to adjust sagittal expansion of the first plate 102 relative to the center body 101, as discussed and illustrated in further detail herein (see sections 1.2 and 2.4).

In addition, the ALIF device 100 includes a plate pin 109 which pivotably couples the center body 101 and the second plate 103 for sagittal adjustment as shown further herein.

TABLE 1

Elements and their corresponding reference numbers.

| "Parent" element | Element | Ref Label |
|---|---|---|
| | ALIF device | 100 |
| ALIF device | coronal adjustment mechanism | 20 |
| | sagittal adjustment mechanism | 30 |
| | center body | 101 |
| | first plate | 102 |
| | second plate | 103 |
| | plate pin | 109 |
| Coronal adjustment mechanism (ALIF device) | coronal advancer screw | 104 |
| | first coronal advancer screw | 104A |
| | second coronal advancer screw | 104B |
| | coronal advancer | 105 |
| | first coronal advancer | 105A |
| | second coronal advancer | 105B |
| | coronal lifter | 106 |
| | first coronal lifter | 106A |
| | second coronal lifter | 106B |
| Sagittal adjustment mechanism (ALIF device) | sagittal advancer screw | 107 |
| | first sagittal advancer screw | 107A |
| | second sagittal advancer screw | 107B |
| | sagittal advancer | 108 |
| | first sagittal advancer | 108A |
| | second sagittal advancer | 108B |
| Center Body (ALIF device) | central access feature | 110 |
| | coronal advancer track | 111 |
| | first coronal advancer track | 111A |
| | second coronal advancer track | 111B |
| | threaded bore element | 112 |
| | dovetail portion | 113 |
| | coronal lifter track | 114 |
| | sagittal advancer track | 115 |
| | first sagittal advancer track | 115A |
| | second sagittal advancer track | 115B |
| | threaded bore element | 116 |
| | dovetail portion | 117 |
| | central cavity | 118 |
| | body pin receptacle | 119 |
| First plate (ALIF device) | upper access feature | 120 |
| | anterior face | 121 |
| | top surface | 123 |
| | central cavity | 124 |
| Second plate (ALIF device) | lower access feature | 130 |
| | anterior face | 131 |
| | screw access apertures | 132 |
| | first screw access aperture | 132A |
| | second screw access aperture | 132B |
| | bottom surface | 133 |
| | central cavity | 134 |
| | plate pin receptacle | 135 |
| | slider tracks | 136 |
| Coronal Advancer (Coronal Adjustment Mechanism) | complementary dovetail portion | 151 |
| | first lumen | 152 |
| | second lumen | 153 |
| | advancer screw seat | 154 |
| | lifter engagement area | 155 |
| | riser wedges | 156 |
| | substrate riser wedges | 157 |
| | winged riser wedges | 158 |
| Coronal Lifter (Coronal Adjustment Mechanism) | top face | 161 |
| | vertical guide tabs | 162 |
| | advancer engagement area | 165 |
| | complementary lifter wedges | 166 |
| | ceiling lifter wedges | 167 |
| | winged lifter wedges | 168 |
| | windows | 169 |

TABLE 1-continued

Elements and their corresponding reference numbers.

| "Parent" element | Element | Ref Label |
|---|---|---|
| Sagittal Advancer (Sagittal Adjustment Mechanism) | complementary dovetail portion | 181 |
| | first lumen | 182 |
| | second lumen | 183 |
| | advancer screw seat | 184 |
| | slider | 185 |
| | applicator device | 200 |
| Applicator Device | member | 202 |
| | distal portion | 204 |
| | proximal portion | 206 |
| | handle | 208 |
| | gearbox | 210 |
| Gearbox (Applicator Device) | saddle portion | 212 |
| | primary gear | 222 |
| | plurality of intermediate gears | 224 |
| | first terminal gear | 226A |
| | second terminal gear | 226B |
| | first driver member | 227A |
| | second driver member | 227B |
| | central driver member | 230 |
| Additional Components for Installation | anchoring screws | 310A-310C |
| | anterior plate | 320 |

1.1 Coronal Expansion Overview

To enable independent expansion of either lateral side of the ALIF device 100 in the coronal plane, the ALIF device 100 includes the coronal adjustment mechanism 20 demonstrated in FIGS. 5A-5F, which includes the coronal advancers 105 in operative association with the coronal lifters 106.

For brevity, the present disclosure will discuss operation of the coronal adjustment mechanism in terms of one coronal advancer-lifter pair associated with one lateral side of the ALIF device 100, e.g., a coronal advancer 105 and a coronal lifter 106; note that the same discussion applies to the other lateral side of the ALIF device 100. Importantly, each coronal advancer-lifter pair independently controls coronal expansion of the ALIF device 100 along the respective lateral side of the ALIF device 100, so that a practitioner can adjust each lateral side independently to accommodate differences in anatomy.

As discussed in further detail herein, the coronal advancer 105 can be positioned along the top portion of the center body 101, and underneath the coronal lifter 106 as shown. Actuation of the coronal advancer 105 in a first direction along the anteroposterior axis (by rotation of a coronal advancer screw 104) expands the ALIF device 100 in the coronal plane by causing the coronal advancer 105 to push the coronal lifter 106 upwards in the coronal plane as shown. In turn, the coronal lifter 106 is positioned along a top portion of the coronal advancer 105 and underneath the first plate 102 (in particular, underneath one lateral side of the first plate 102 as shown). As the coronal advancer 105 pushes the coronal lifter 106 upwards in the coronal plane, the coronal lifter 106 likewise pushes its lateral side of the first plate 102 upwards in the coronal plane. An example of this operation is shown in FIGS. 5E and 5F.

Notably, the coronal advancer 105 engages a coronal advancer track 111 of the center body 101, and simultaneously engages the coronal lifter 106 to enable coronal plane adjustment while minimizing a starting height of the ALIF device 100. Advancement of the coronal advancer 105 along the coronal advancer track 111 of the center body 101 (by rotation of the coronal advancer screw as shown in FIGS. 5E and 5F) causes the coronal advancer 105 to push the coronal lifter 106 upwards. As shown in FIG. 5F and as discussed in further detail herein, the coronal advancer 105 includes coronal riser wedges that interface with complementary coronal lifter wedges of the coronal lifter 106 such that advancement of the coronal advancer 105 in a first direction along the anteroposterior axis ("X" in FIG. 5F) results in actuation of the coronal lifter 106 in a first direction along the craniocaudal axis ("Y" in FIG. 5F). Note that actuating the coronal advancer 105 in a second direction along the anteroposterior axis opposite from the first direction (i.e., "−X") when under a compressive force when implanted as shown in FIGS. 1A and 1B results in actuation of the coronal lifter 106 in a second direction along the craniocaudal axis ("−Y" in FIG. 5F).

1.2 Sagittal Expansion Overview

To enable independent expansion in the sagittal plane, the ALIF device 100 includes the sagittal adjustment mechanism demonstrated in FIGS. 6A-6F, which includes the one or more sagittal advancers 108 in operative association with the second plate 103.

For brevity, the present disclosure will discuss operation of one sagittal advancer 108 associated with one lateral side of the ALIF device 100; note that the same discussion applies to the other lateral side of the ALIF device 100.

Figure 6A:
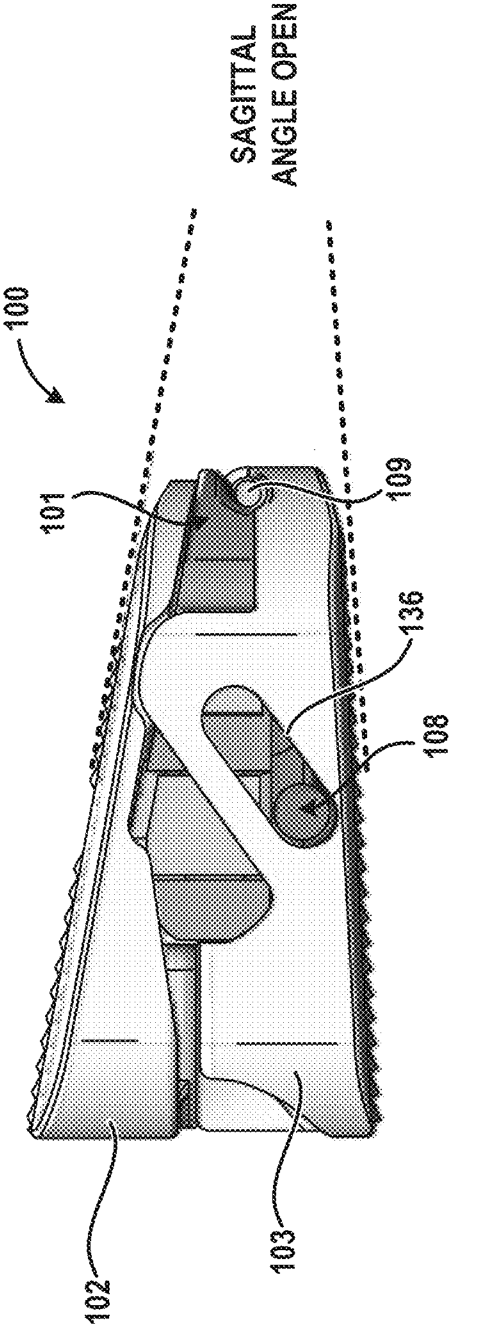
FIGS. 6A-6F are a series of illustrations showing sagittal adjustment of an expandable ALIF device.
Figure 6B:
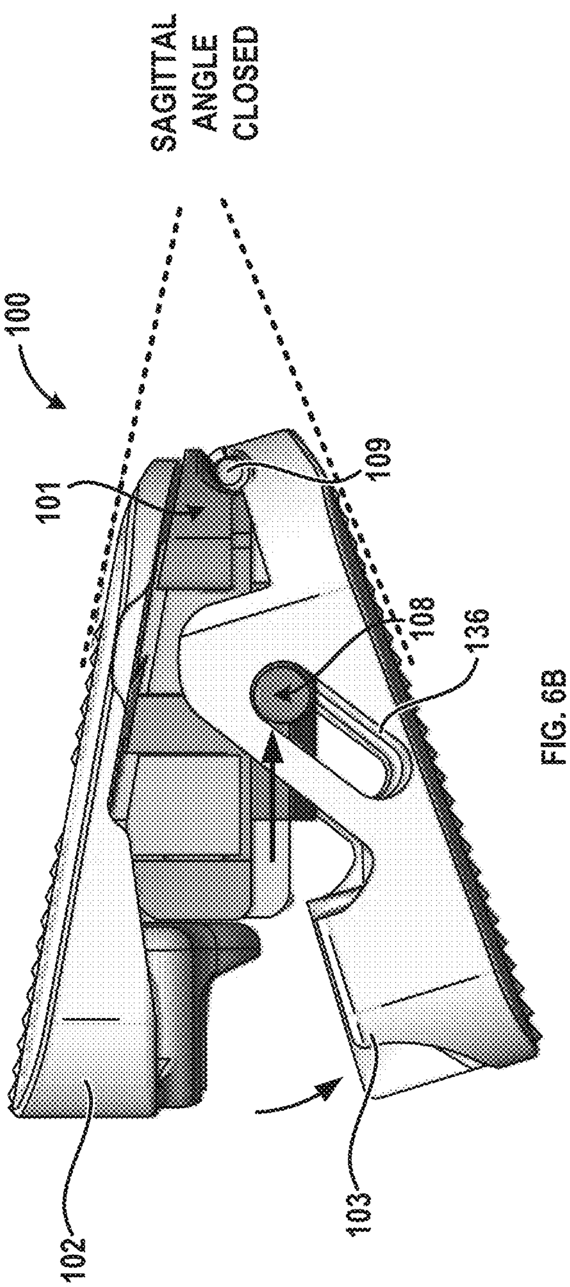
Figure 6C:
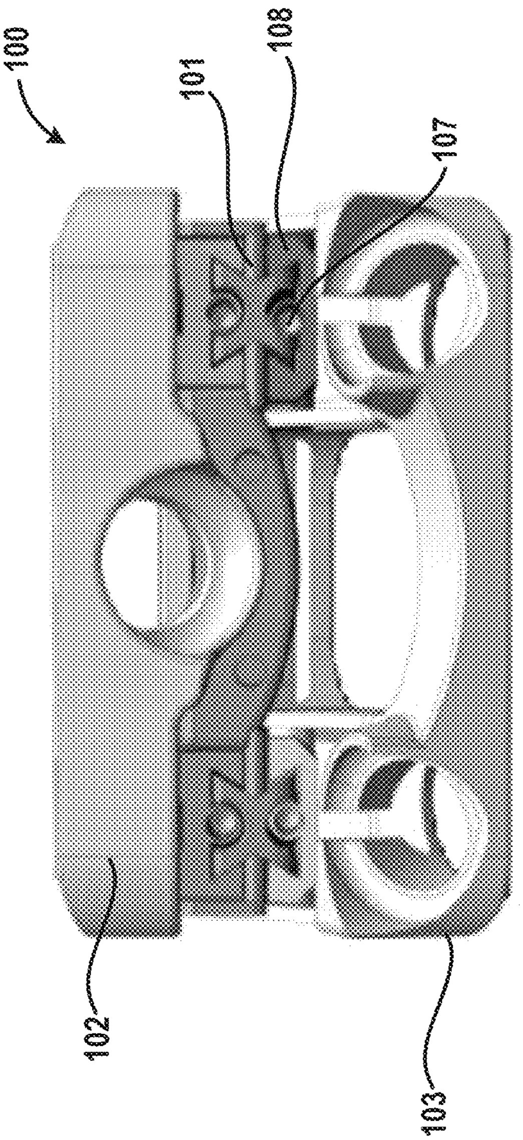
Figure 6D:
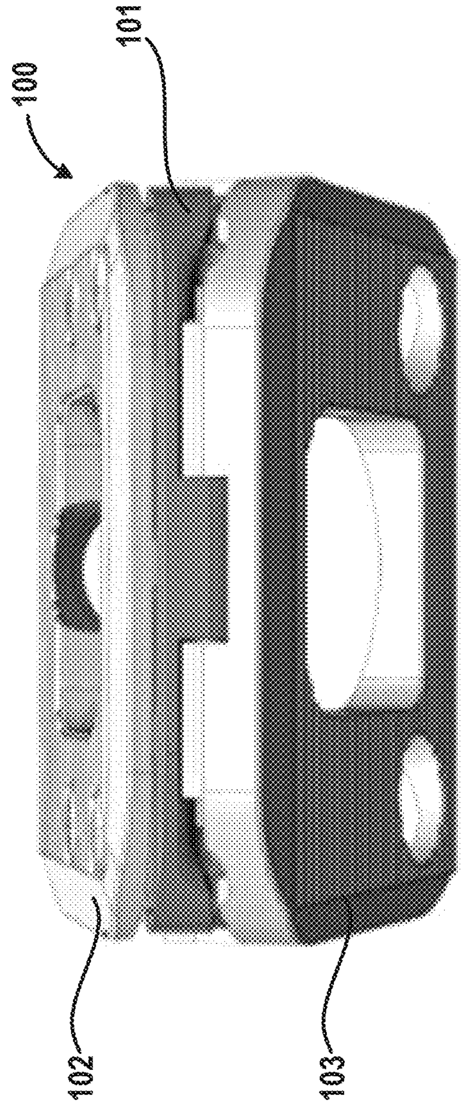
Figure 6E:
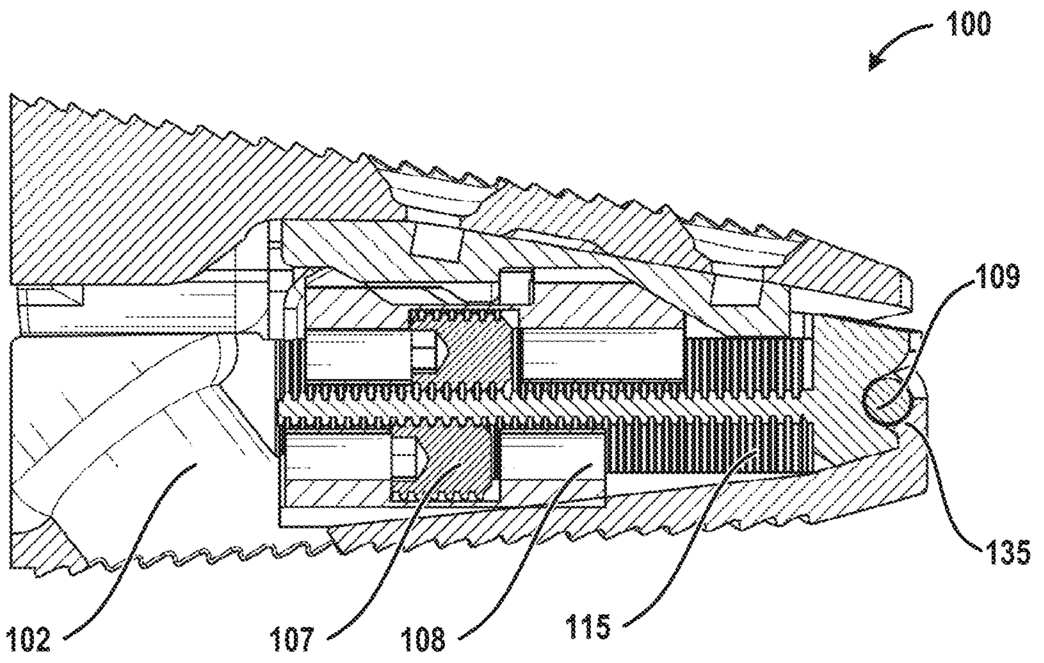
Figure 6F:
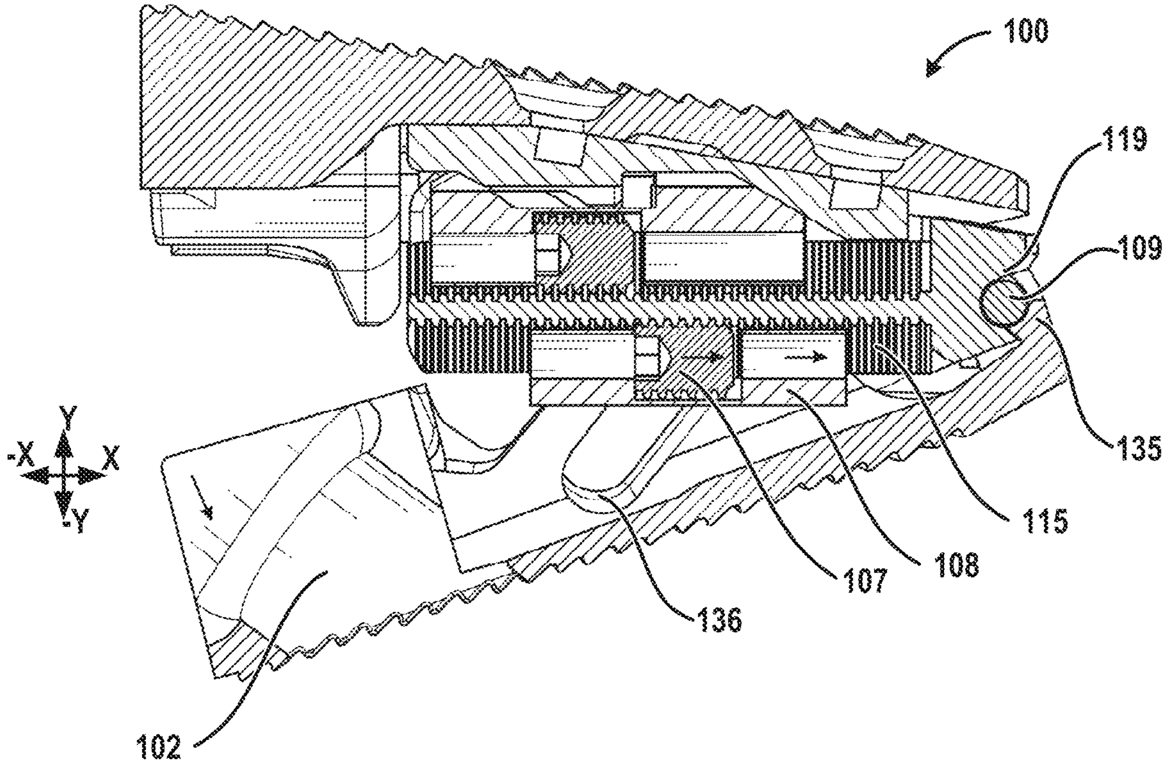

As discussed in further detail herein, the sagittal advancer 108 can be positioned along the bottom portion of the center body 101, and above the second plate 103 as shown. The second plate 103 can be rotatably coupled to a posterior portion of the center body 101 by the plate pin 109. Actuation of the sagittal advancer 108 in a first direction along the anteroposterior axis (by rotation of a sagittal advancer screw 107) expands the ALIF device 100 in the sagittal plane by causing the sagittal advancer 108 to push an anterior portion of the second plate 103 downward relative to the center body 101 (while the posterior portion of the second plate 103 remains coupled to the center body 101 by the plate pin 109). An example of this operation is shown in FIGS. 6E and 6F. This action increases an angle formed between the first plate 102 and the second plate 103 as shown.

Notably, sagittal advancer 108 engages a sagittal advancer track 115 of the center body 101 and a slider track of the second plate 103 to enable sagittal plane adjustment while minimizing a starting height of the ALIF device 100. In particular, as shown in FIGS. 6A and 6B, as well as FIGS. 6E and 6F, advancement of the sagittal advancer 108 in a first direction along the anteroposterior axis ("X" in FIG. 6F) along a sagittal advancer track 115 of the center body 101 (FIGS. 6E and 6F) causes the sagittal advancer 108 to rotate the anterior portion of the second plate 103 in the second direction along the craniocaudal axis ("−Y" in FIG. 6F) due to the engagement of the sagittal advancer with the slider track of the second plate 103 (FIGS. 6A and 6B). Note that actuating the sagittal advancer 108 in the second direction along the anteroposterior axis opposite from the first direction (i.e., "−X") when under a compressive force when implanted as shown in FIGS. 1A and 1B results in rotation of the anterior portion of the second plate 103 in the first direction along the craniocaudal axis ("Y").

Further, a posterior portion of the second plate 103 includes a plate pin receptacle 135 that aligns with a body pin receptacle 119 of the center body 101 for rotatably coupling the posterior portion of the second plate 103 with the center body 101 by the plate pin 109 as shown in FIGS. 6E and 6F.

The coronal advancer 105 and the sagittal advancer 108 can each be independently actuated using an applicator device, as discussed in further detail herein.

1.3 Organizational Overview

The remainder of the disclosure is organized as follows:

Section 2 outlines individual features of the components of the ALIF device 100. In particular, section 2.1 outlines features of the center body 101 of the ALIF device 100. Section 2.2 outlines features of the first plate 102 and the second plate 103 of the ALIF device 100. Section 2.3 outlines features of the coronal adjustment mechanism 20 of the ALIF device 100. Section 2.4 outlines features of the sagittal adjustment mechanism 30 of the ALIF device 100.

Section 3 outlines an applicator device and fusion system of the ALIF device 100. Section 4 describes functional operation of the individual features of the ALIF device 100 outlined in Section 2. In particular, section 4 outlines methods of insertion and use of the coronal adjustment mechanism 20 (section 4.1, pertaining to the coronal advancer 105, the coronal lifter 106, and the first plate 102) and the sagittal adjustment mechanism 30 (section 4.2, pertaining to the sagittal advancer 108 and the second plate 103).

2. Features of Various Components of the ALIF Device 2.1 Center Body

Figure 7A:
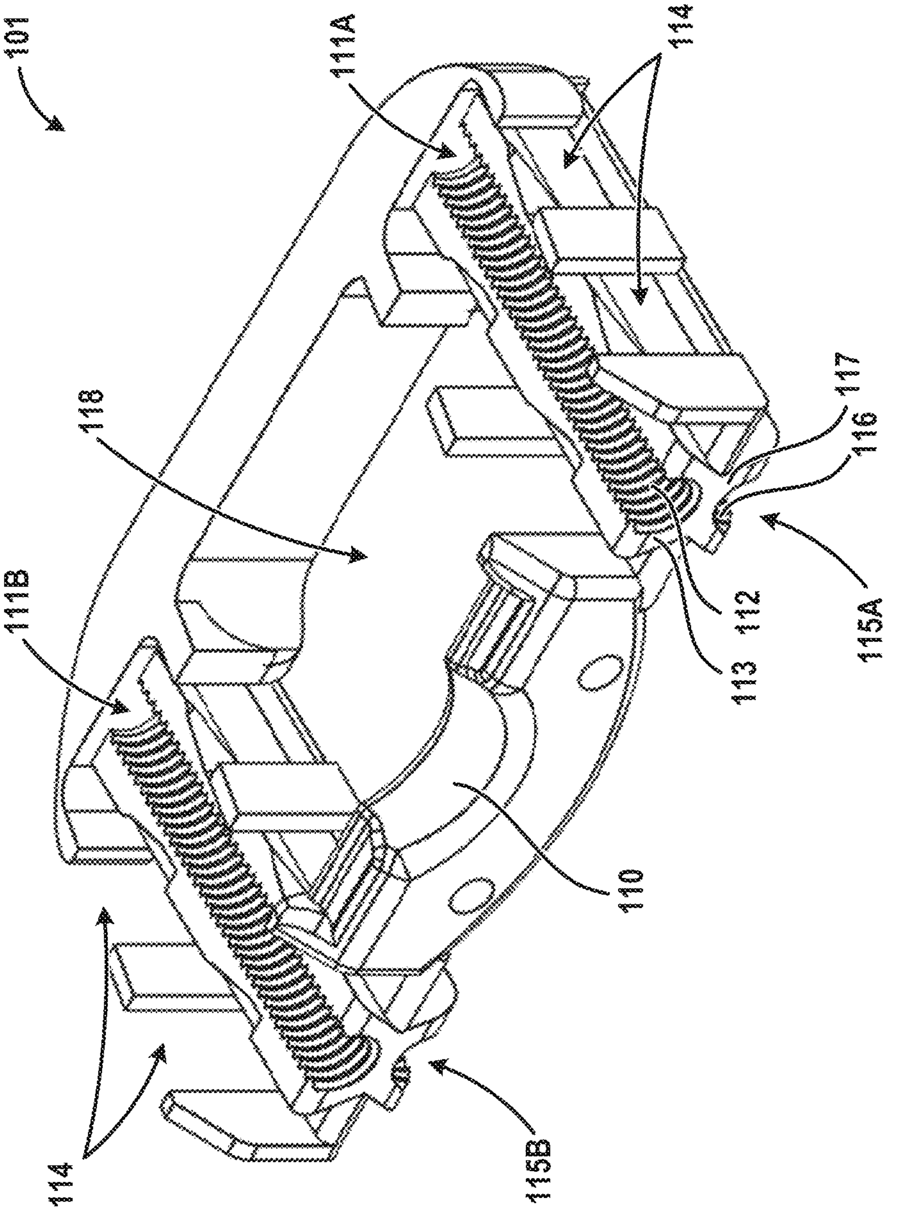
FIGS. 7A-7G are a series of illustrations showing assembly of an expandable ALIF device.

FIG. 7A shows the center body 101 of the ALIF device 100. The center body 101 provides a base structure for engagement of other components of the ALIF device 100, as demonstrated sequentially in FIGS. 7B-7G. For brevity, the present disclosure will discuss operation of components associated with one lateral side of the ALIF device 100; note that the same discussion applies to the other lateral side of the ALIF device 100.

Figure 7C:
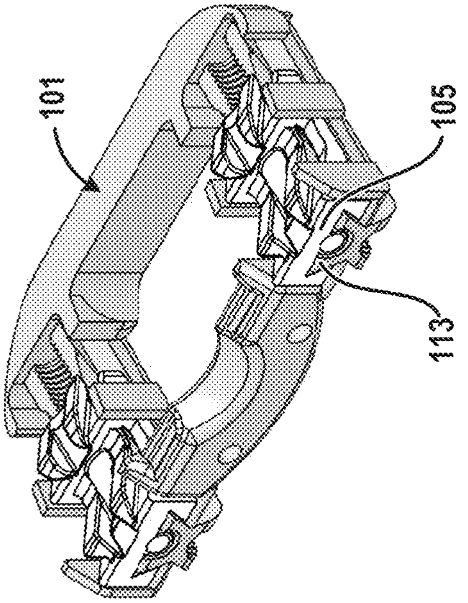
Figure 7B:
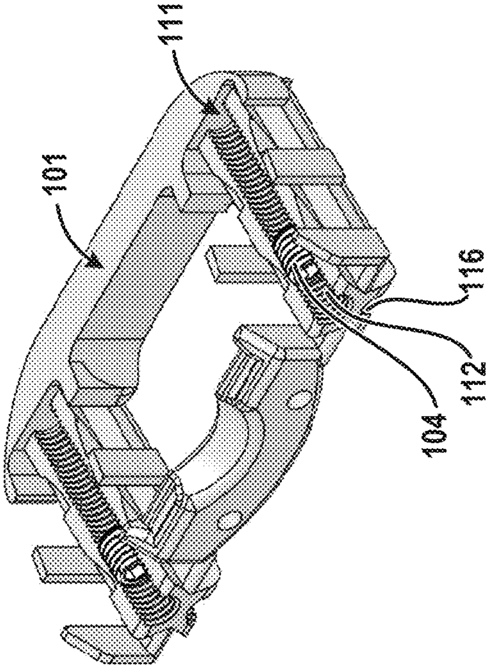

In particular, the top surface of the center body 101 includes the coronal advancer track 111 for engagement with the coronal advancer 105 (in particular, a first coronal advancer track 111A along a first lateral side of the center body 101 for engagement with the first coronal advancer 105A and first coronal advancer screw 104A, and a second coronal advancer track 111B along a second lateral side of the center body 101 for engagement with the second coronal advancer 105B and second coronal advancer screw 104B). Importantly, the coronal advancer track 111 includes a threaded bore element 112 that receives the coronal advancer screw 104 as shown in FIG. 7B. In the illustrated example, the coronal advancer track 111 further includes a dovetail portion 113 that secures the coronal advancer 105 along the center body 101 as shown in FIG. 7C (e.g., by receiving a complementary dovetail portion 151 of the coronal advancer 105 labeled in FIG. 8A).

Figure 7D:
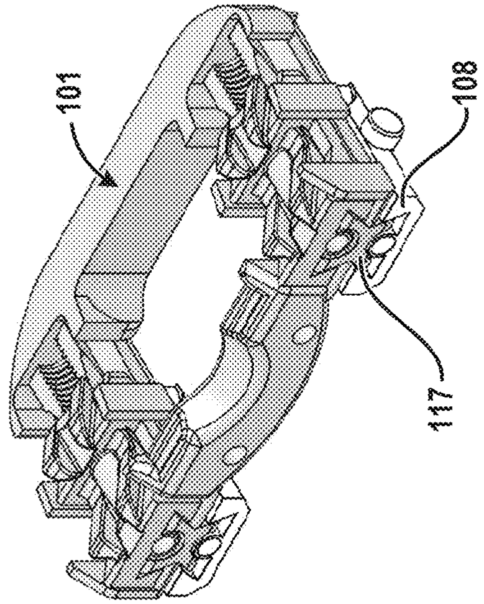

A bottom surface of the center body 101 includes a sagittal advancer track 115 for engagement with the sagittal advancer 108 as shown in FIG. 7D (in particular, a first sagittal advancer track 115A along a first lateral side of the center body 101 for engagement with the first sagittal advancer 108A and a second sagittal advancer track 115B along a second lateral side of the center body 101 for engagement with the second sagittal advancer 108B). Importantly, the sagittal advancer track 115 includes a threaded bore element 116 that receives a sagittal advancer screw 107. In the illustrated example, the sagittal advancer track 115 further includes a dovetail portion 117 that secures the sagittal advancer 108 along the center body 101 as shown (e.g., by receiving a complementary dovetail portion 181 of the sagittal advancer 108 labeled in FIG. 12A). Each sagittal advancer track 115 can be positioned directly below a corresponding coronal advancer track 111 in a mirrored arrangement as shown.

Figure 7F:
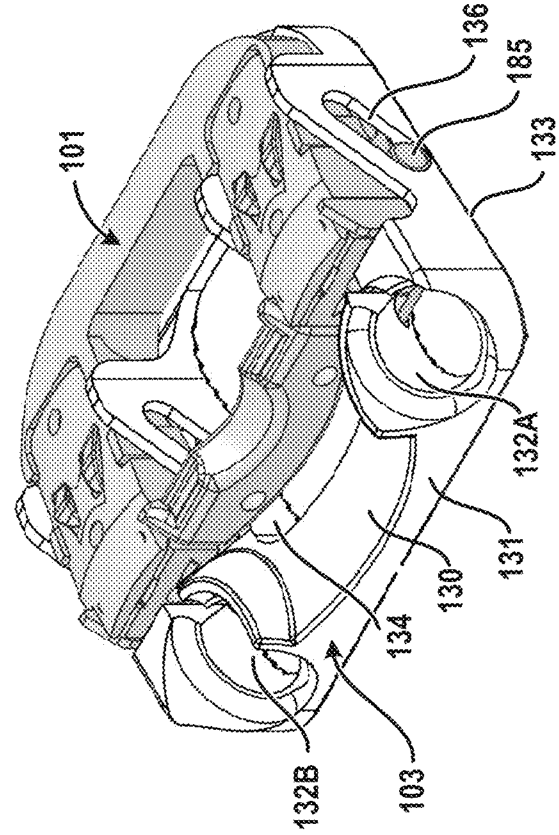
Figure 7E:
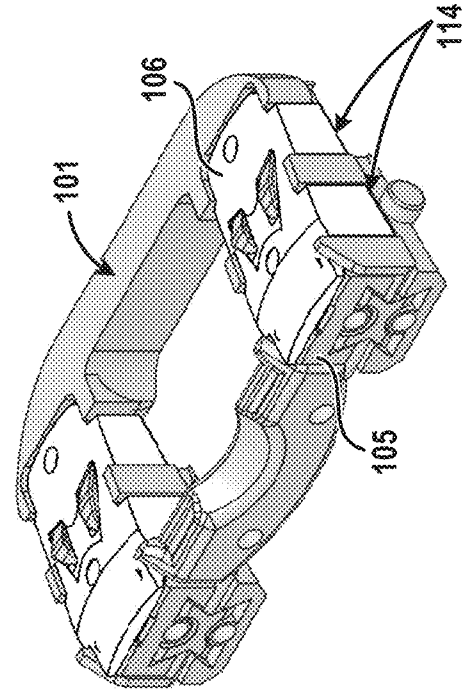

Further, as shown in FIG. 7E, the center body 101 includes a coronal lifter track 114 for engagement with the coronal lifter 106 (in particular, one or more coronal lifter tracks 114 along exterior to each coronal advancer 105). Each coronal lifter track 114 flanks either side of the associated coronal advancer track 111 as shown. As shown in FIG. 7E, the coronal lifter 106 encapsulates the coronal advancer 105 when engaged with the coronal lifter track 114 of the center body 101. Each coronal lifter track 114 ensures that motion of the coronal lifter 106 is restricted to a direction that is normal to a (transverse) plane defined by the center body 101 when the coronal lifter 106 is actuated by the coronal advancer 105 as discussed in greater detail herein (such an example is shown in FIGS. 5E, 5F, 10A, and 10B).

Figure 5A:
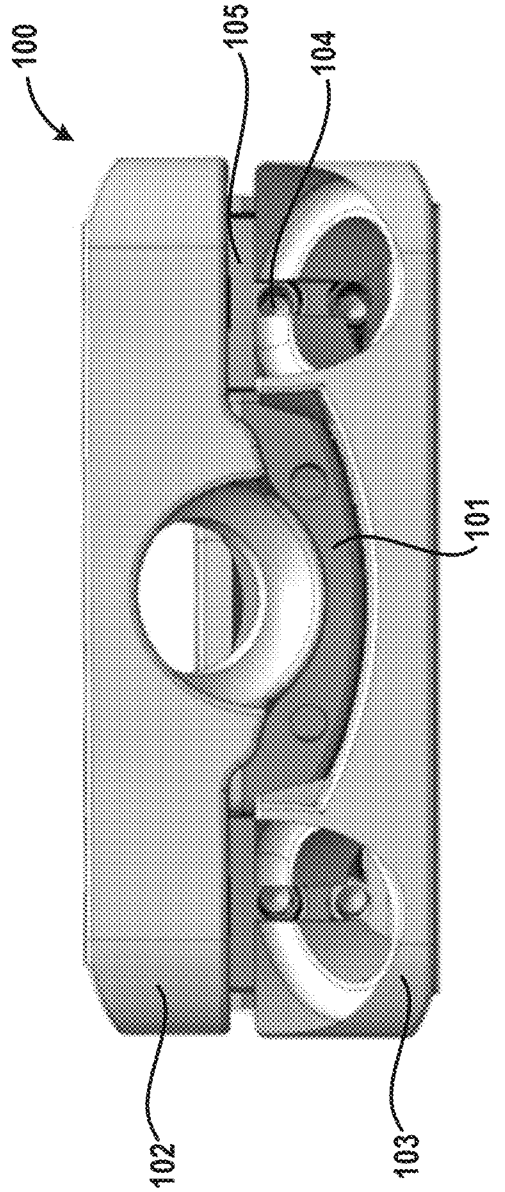
FIGS. 5A-5F are a series of illustrations showing coronal adjustment of an expandable ALIF device.
Figure 5B:
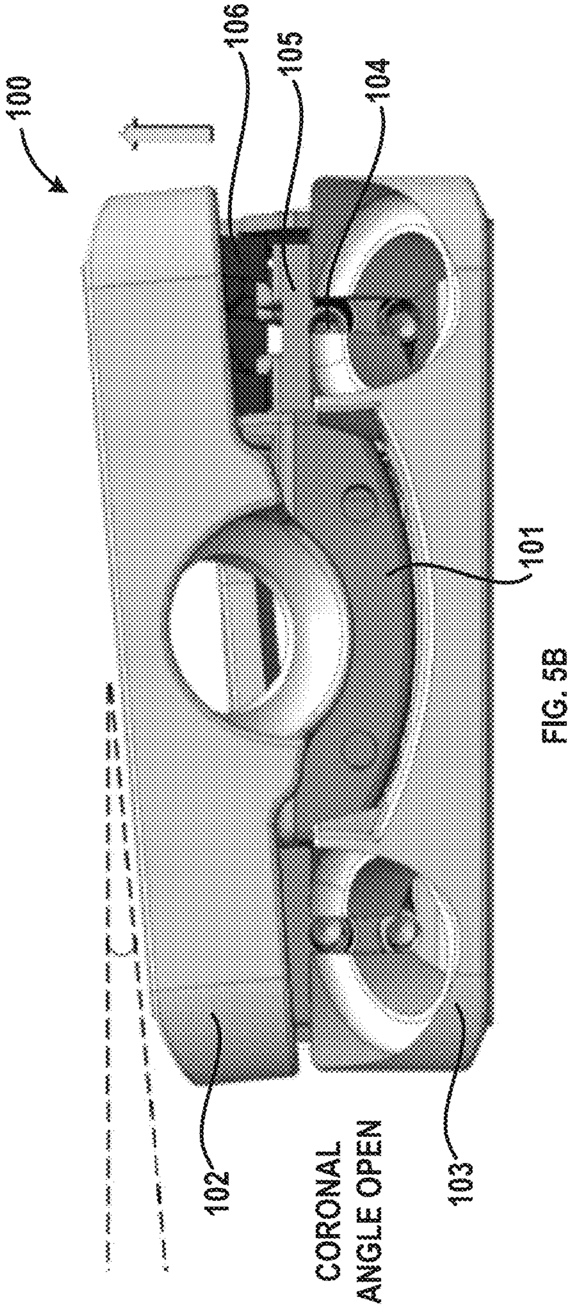
Figure 5C:
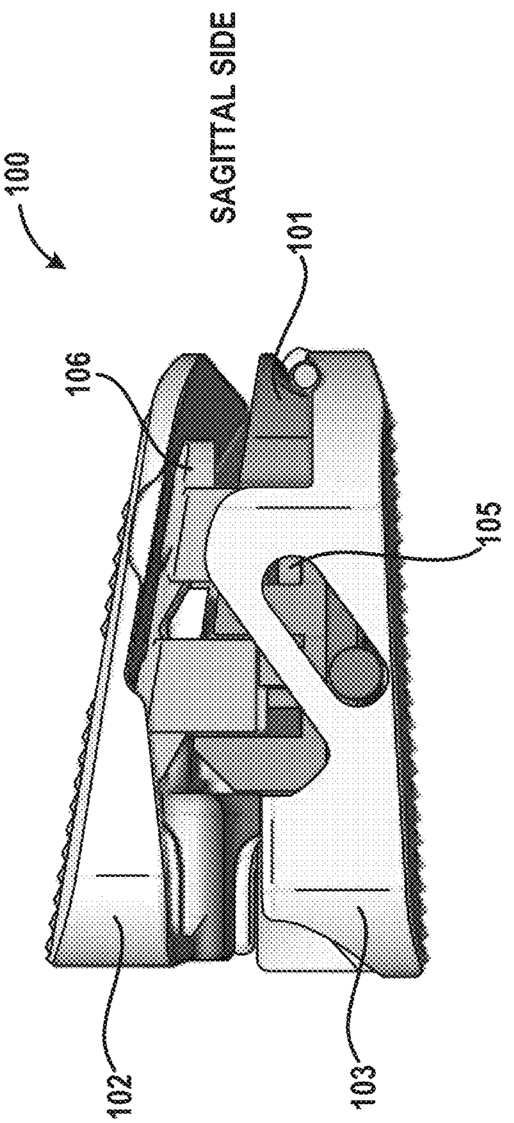
Figure 5D:
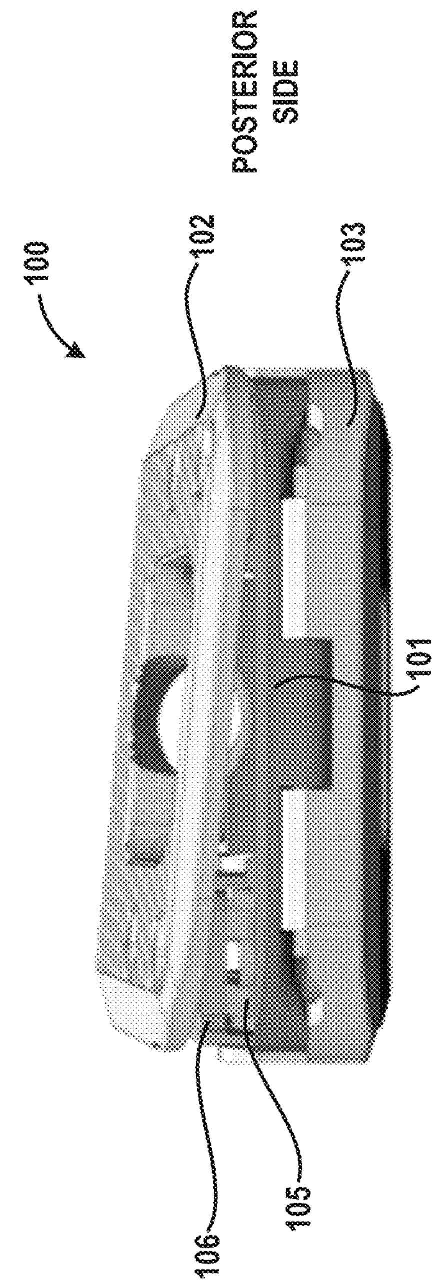
Figure 5E:
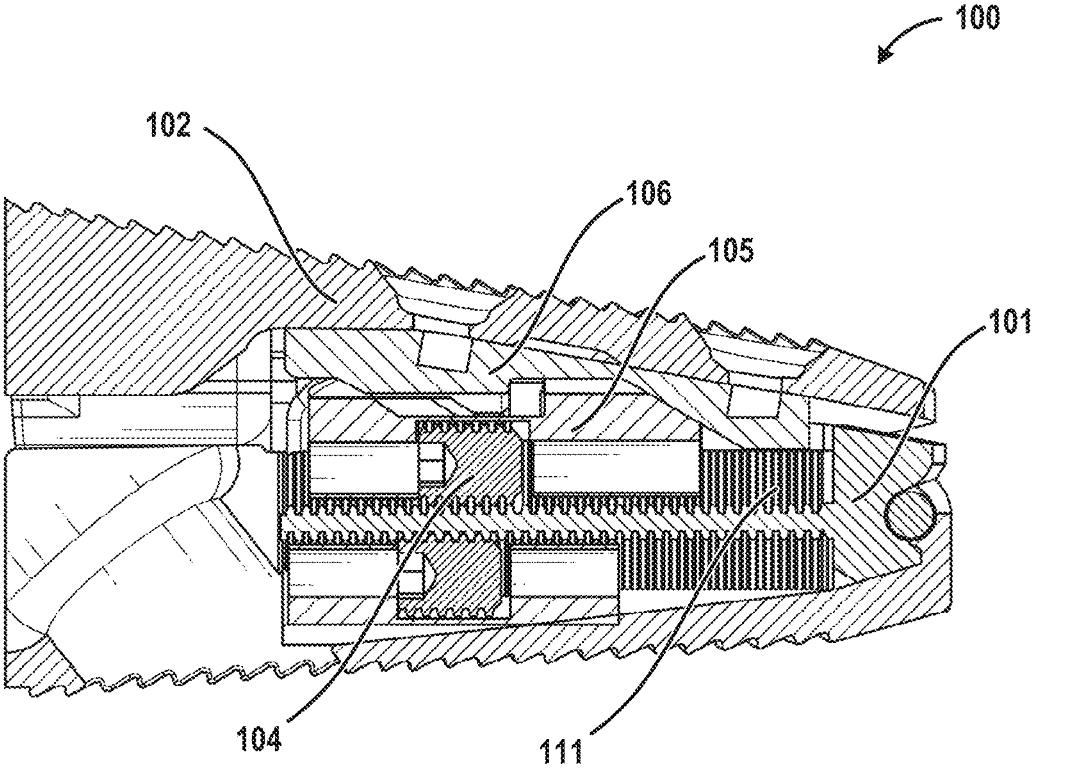
Figure 5F:
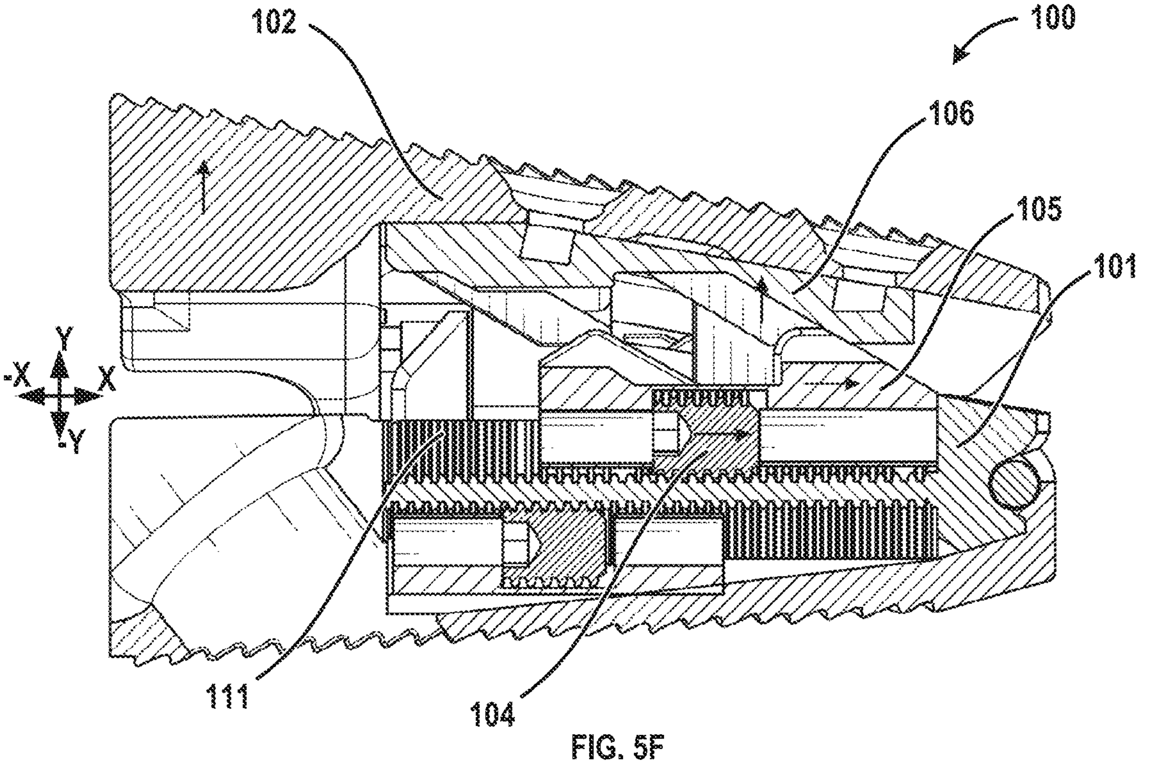

Further, the center body 101 can include a central cavity 118, which can be positioned between the first coronal advancer track 111A and the second coronal advancer track 111B as illustrated in FIG. 5A. In some examples, the central cavity 118 can receive bone graft material.

Additional features of the center body 101 can include a central access feature 110 defined along an anterior portion of the center body 101 for engagement with an applicator device, which can be removably coupled to the center body 101.

2.2 First and Second Plates

Figure 7G:
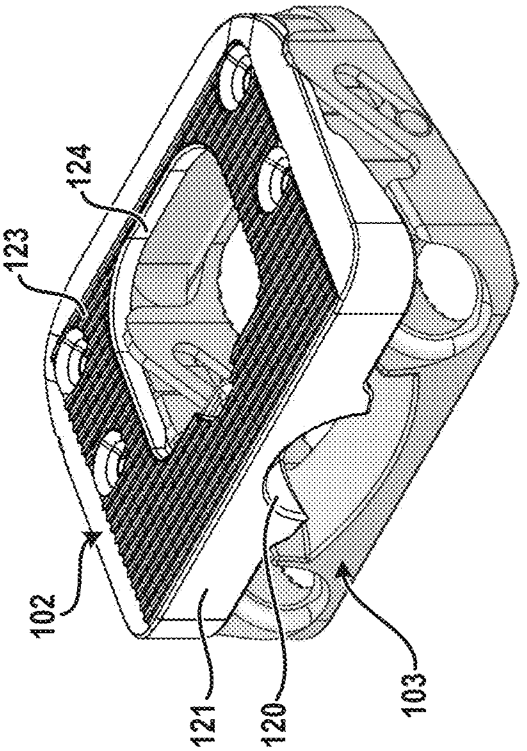

FIGS. 7F and 7G respectively show engagement of the second plate 103 (FIG. 7F) and the first plate 102 (FIG. 7G) to the center body 101. The first plate 102 and the second plate 103 are each configured to contact respective first and second vertebrae when the ALIF device 100 is inserted therebetween. The first plate 102 and the second plate 103 can be individually actuated by a practitioner to a targeted coronal and/or sagittal configuration by the coronal adjustment mechanism 20 and the sagittal adjustment mechanism 30 outlined herein.

The first plate 102 rests above the center body 101 and encapsulates the coronal advancer 105 and the coronal lifter 106 between the first plate 102 and the center body 101. As shown in FIG. 7G, the first plate 102 includes an anterior face 121 which can include an upper access feature 120 that aligns with the central access feature 110 of the center body 101 for receipt of an anchoring screw that engages the first plate 102 with the first vertebra 2 (FIGS. 1A and 1B). A top surface 123 of the first plate 102 defines a first textured face that engages an underside of the first vertebra 2. Further, the first plate 102 can include a central cavity 124 that communicates with the central cavity 118 of the center body 101.

In some examples, as shown in FIGS. 5E and 5F, the first plate 102 and coronal lifter 106 each include holes that align with one another for receipt of screws for coupling the first plate 102 and coronal lifter 106 together.

The second plate 103 rests below the center body 101 and encapsulates the sagittal advancer 108 between the second plate 103 and the center body 101. As shown in FIG. 7F, the second plate 103 includes an anterior face 131 which can include screw access apertures (e.g., first screw access aperture 132A associated with the first lateral side of the ALIF device 100 and second screw access aperture 132B associated with the second lateral side of the ALIF device 100). The screw access apertures serve a dual purpose of providing a path for insertion of an applicator device, as well as receiving anchoring screws for engagement with the second vertebra. A bottom surface 133 (FIG. 7F) of the second plate 103 defines a second textured face (visible in FIG. 3C) that engages a top side of the second vertebra 4 (FIGS. 1A and 1B). Further, the second plate 103 can include a central cavity 134 that communicates with the central cavity 118 of the center body 101, as well as a lower access feature 130 that aligns with the central access feature 110 and the upper access feature 120 to collectively accommodate insertion of an applicator device and other tools. A posterior portion of the center body 101 can also include a body pin receptacle 119 (visible in FIG. 6F), which can engage the plate pin 109 for rotatably coupling the center body 101 to the second plate 103 as discussed in further detail herein.

Importantly, as shown in FIG. 7F as well as FIGS. 6A and 6B, the second plate 103 also includes slider tracks 136 that engage with respective sliders 185 of the sagittal advancers 108 in a “pin and slot” arrangement described further herein (section 2.4). In the examples shown, the second plate 103 includes four slider tracks 136: one for each slider 185 of the sagittal advancers 108. The slider tracks 136 are angled such that actuation of the sagittal advancer 108 along the sagittal advancer track 115 causes the anterior portion of the second plate 103 to rotate about the plate pin 109 and increase or decrease an angle between the second plate 103 and the first plate 102. In the example shown, a first end of each slider track 136 is at a “lower” position than a second end of the corresponding slider track 136 (a first portion of the slider track 136 corresponding with a first position of the slider 185 of the sagittal advancer 108 is located inferior to a second portion of the slider track 136 corresponding with a second position first position of the slider 185 of the sagittal advancer 108).

2.3 Coronal Adjustment Mechanism

As discussed above with reference to FIGS. 5A-5F, the coronal adjustment mechanism of the ALIF device 100 includes the coronal advancer 105 which engages a top portion of the center body 101, as well as the coronal lifter 106 which rests above the coronal advancer 105 and serves to lift the first plate 102 along the craniocaudal axis as the coronal advancer 105 moves along the anteroposterior axis. Actuation of the coronal advancer 105 along the coronal advancer track 111 of the center body is controlled by the coronal advancer screw 104 captured along a bottom portion of the coronal advancer 105, which engages the center body 101 at the threaded bore element 112 of the coronal advancer track 111. Rotation of the coronal advancer screw 104 within the threaded bore element 112 causes translation of the coronal advancer 105 along the coronal advancer track 111 of the center body 101 (following anteroposterior axis “X”).

The arrangement of the coronal advancer 105 and coronal advancer track 111, as well as of the coronal advancer 105 and coronal lifter 106, collectively minimize a starting height of the ALIF device 100 while ensuring structural stability and allowing fine-tuning of the coronal adjustment provided by the ALIF device 100.

2.3.1 Coronal Advancer

Figure 8A:
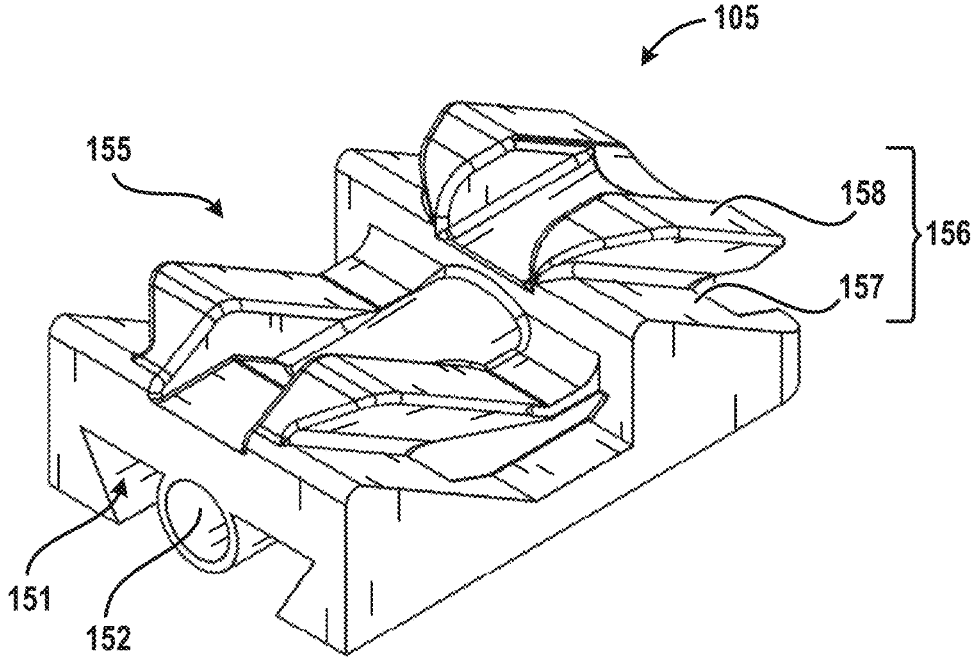
FIGS. 8A and 8B are a pair of illustrations showing a coronal advancer for coronal expansion of an expandable ALIF device, where
Figure 8B:
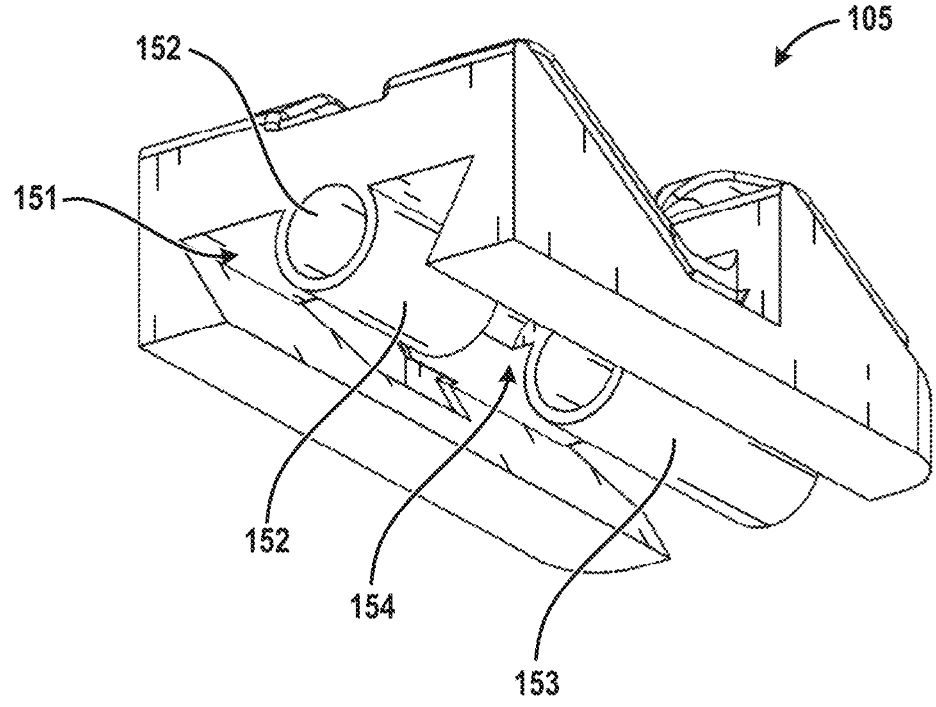

FIGS. 8A and 8B show top perspective and bottom perspective views of the coronal advancer 105. A bottom portion of the coronal advancer 105 includes a complementary dovetail portion 151 that engages the dovetail portion 113 of the coronal advancer track 111 as discussed above with reference to FIG. 7C. Within the complementary dovetail portion 151, the coronal advancer 105 includes one or more lumens (e.g., a first lumen 152 and a second lumen 153), and an advancer screw seat 154 for capture of the coronal advancer screw 104. The first lumen 152 is hollow, allowing insertion of an applicator device through the first lumen 152 to engage and rotate the coronal advancer screw 104. Note that while the example of FIG. 8B shows the second lumen 153, this component need not be a hollow lumen; it just needs to capture the coronal advancer screw 104. Rotation of the coronal advancer screw 104 causes translation of the coronal advancer 105 along a direction of elongation of the coronal advancer track 111 (i.e., the anteroposterior axis) as discussed in further detail herein.

A top portion of the coronal advancer 105 defines a lifter engagement area 155 that engages the coronal lifter 106. In particular, the lifter engagement area 155 can include one or more riser wedges 156 that engage an underside of the coronal lifter 106 and push the coronal lifter 106 along a craniocaudal axis as the coronal advancer 105 is actuated along the coronal advancer track 111. In the examples shown, the riser wedges 156 are angled in such a way that a first end of a riser wedge 156 pointing towards an anterior portion of the coronal advancer 105 is "higher" than a second end of the riser wedge 156 pointing towards a posterior portion of the coronal advancer 105. Such an example is shown in FIGS. 8A and 8B, where the riser wedge 156 is of a generally sawtooth shape having a peak portion and a ramp portion, the peak portion being located anterior to the ramp portion. The shape of the riser wedge 156 when engaged with the coronal lifter 106 allows more force distribution and increases stability.

As shown in FIG. 8A, the riser wedges 156 of the coronal advancer 105 can include more than one type: substrate riser wedges 157 which are formed from a body of the coronal advancer 105; and winged riser wedges 158 which extend from the body of the coronal advancer 105 (like "wings") as shown in FIG. 8A. Generally, the riser wedges 156 of the coronal advancer 105 engage the coronal lifter 106 in a dovetail arrangement as demonstrated further herein (see FIG. 10C, not to be confused with engagement of the coronal advancer 105 and the center body 101 which leverages a different dovetail arrangement).

2.3.2 Coronal Lifter

FIGS. 9A-9D show the coronal lifter 106, which engages the coronal advancer 105 and pushes the first plate 102 upward in the coronal plane upon actuation of the coronal advancer 105 along the coronal advancer track 111 (demonstrated in FIGS. 5A-5F). Starting with FIG. 9A, the coronal lifter 106 includes a top face 161 that contacts an underside of the first plate 102 such that as the coronal advancer 105 pushes the coronal lifter 106 upward, the coronal lifter 106 concurrently pushes the first plate 102 upward. In some examples, the top face 161 can include screw holes that align with screw holes of the first plate 102 to affix the first plate 102 to the coronal lifter 106.

Further, the coronal lifter 106 includes one or more vertical guide tabs 162 that engage the coronal lifter tracks 114 of the center body 101 (shown in FIG. 7E). When engaged with the coronal advancer 105 and the center body 101, the vertical guide tabs 162 can extend downward around lateral sides of the coronal advancer 105 and insert into the coronal lifter tracks 114 of the center body 101. The engagement of the vertical guide tabs 162 and coronal lifter tracks 114 ensure that as the coronal advancer 105 moves along the coronal advancer track 111 and pushes the coronal lifter 106 upward as shown in the example of FIGS. 5E and 5F, the coronal lifter 106 maintains its original position within the transverse plane while moving upward along the craniocaudal axis (i.e., motion of the coronal lifter 106 is restricted to a direction that is normal to a plane defined by the center body 101).

The coronal lifter 106 rests above the coronal advancer 105, and a bottom surface of the coronal lifter 106 includes an advancer engagement area 165 that engages the lifter engagement area 155 of the coronal advancer 105. In particular, the lifter engagement area 155 can include one or more complementary lifter wedges 166 that engage respective riser wedges 156 of the coronal advancer 105 so that actuation of the coronal advancer 105 along the coronal advancer track 111 pushes the coronal lifter 106 upward. In the examples shown, the complementary lifter wedges 166 are angled in such a way that a first end of each complementary lifter wedge 166 pointing towards an anterior portion of the coronal lifter 106 is "higher" than a second end of the complementary lifter wedge 166 pointing towards a posterior portion of the coronal lifter 106. The shape of the complementary lifter wedge 166 allows more force distribution and increases stability.

Figure 9A:
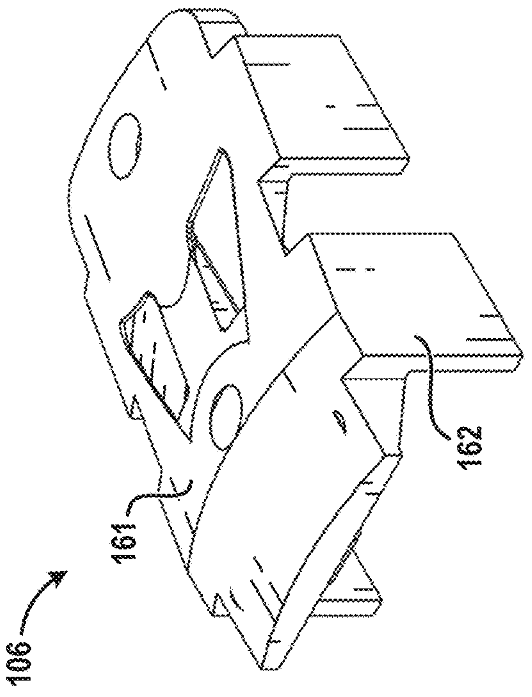
FIGS. 9A-9D are a series of illustrations showing a coronal lifter of an expandable ALIF device where
Figure 9B:
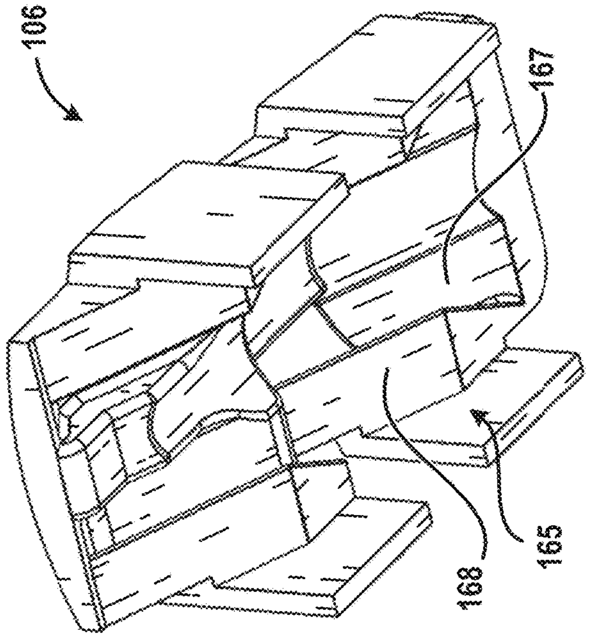
Figure 9C:
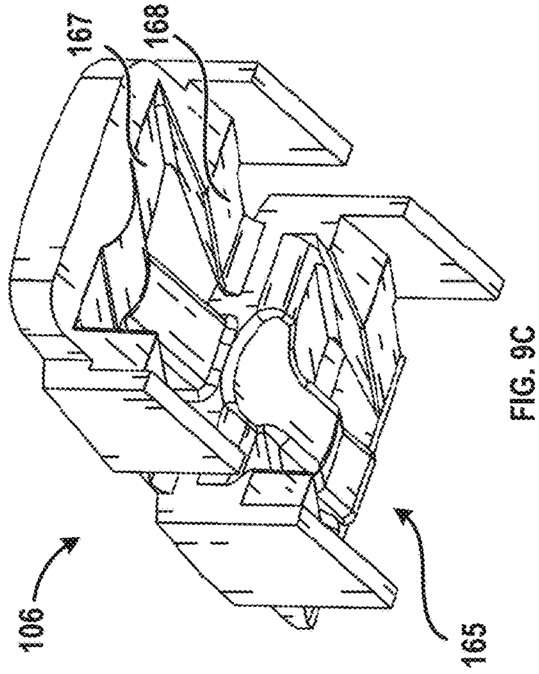
Figure 9D:
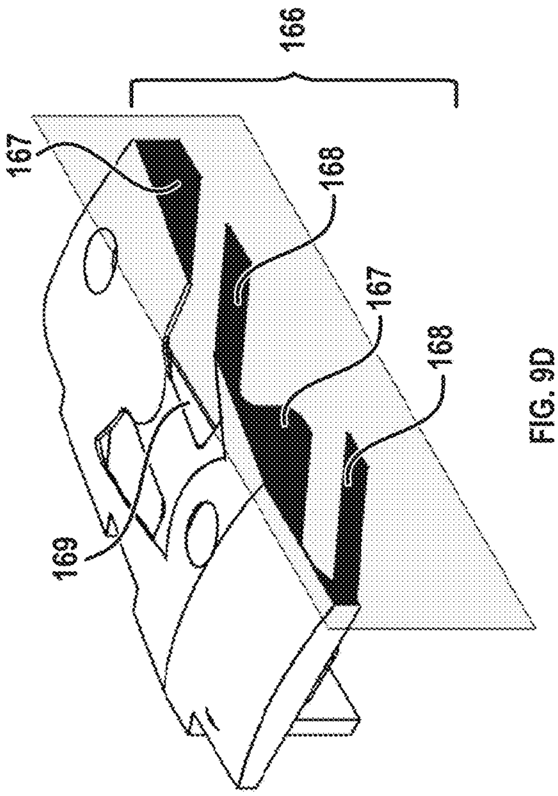

As shown in FIGS. 9B-9D (with FIG. 9B being an anterior below perspective view, FIG. 9C being a posterior below perspective view, and FIG. 9D being a cutaway perspective view correlating with the anterior perspective view of FIG. 9A), the complementary lifter wedges 166 of the coronal lifter 106 can include two types: ceiling lifter wedges 167 which are formed from a body of the coronal lifter 106; and winged lifter wedges 168 which extend from the body of the coronal lifter 106 as shown. Generally, the complementary lifter wedges 166 of the coronal lifter 106 engage the coronal advancer 105 in a dovetail arrangement as previously mentioned and as demonstrated further herein (see FIG. 10C, not to be confused with engagement of the coronal advancer 105 and the center body 101, which also leverages a dovetail arrangement). Further, in some examples, the coronal lifter 106 can include one or more lifter windows 169 along the top face 161 that accommodate the winged riser wedges 158 of the coronal advancer 105 in order to: 1) enable a more compact height of the ALIF device 100; 2) allow pressure equalization when advancing the coronal advancer 105; and 3) reduce an overall weight of the ALIF device 100.

Further, as discussed, each coronal lifter 106 is positioned underneath a first lateral side or a second lateral side of the first plate 102. As such, a height of the first lateral side and the second lateral side of the first plate 102 can be independently adjusted by rotating the coronal advancer screw 104 that corresponds with the appropriate coronal lifter 106.

2.3.3 Engagement of Coronal Advancer and Coronal Lifter

Figure 10C:
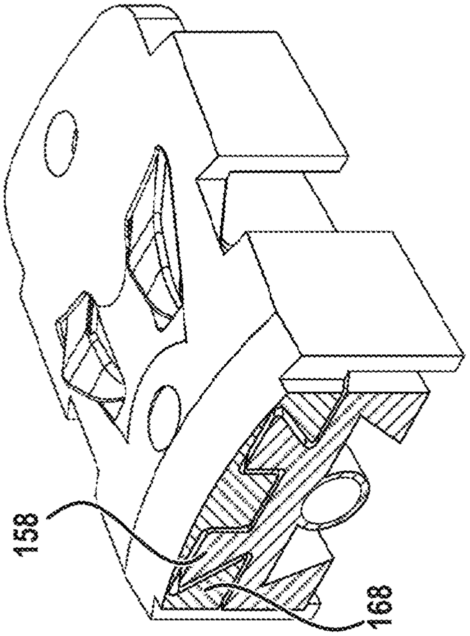
FIGS. 10A-10C are a series of illustrations showing engagement of a coronal advancer and a coronal lifter of an expandable ALIF device, where
Figure 10A:
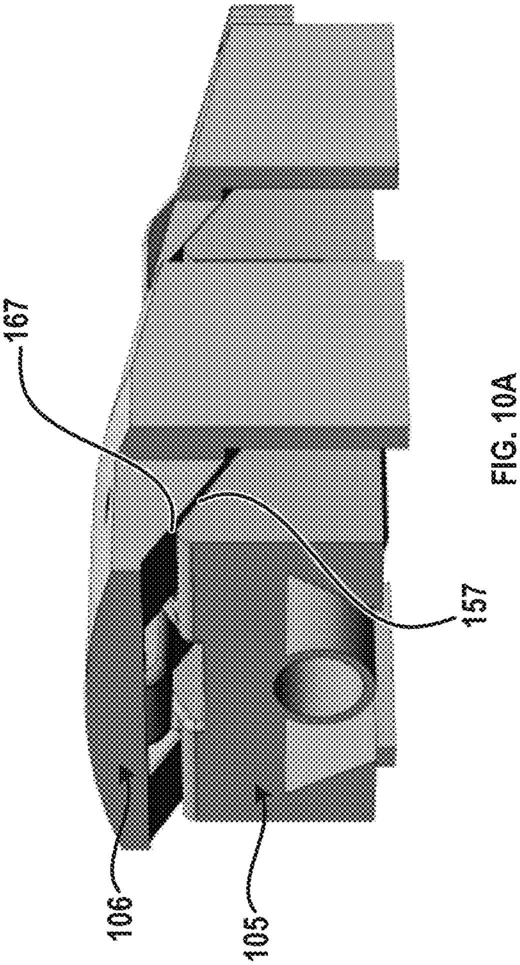
Figure 10B:
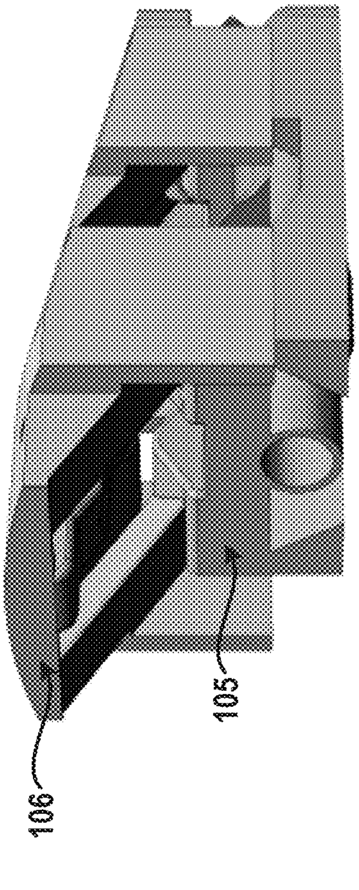
Figure 11A:
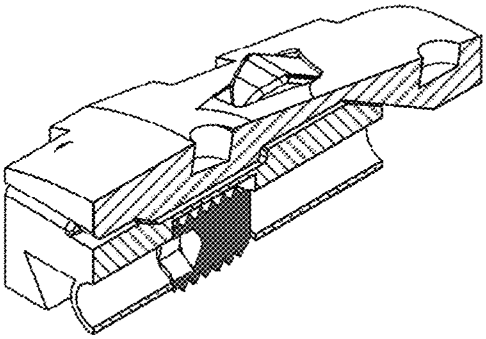
FIGS. 11A-11H are a series of illustrations showing sequential cutaway views demonstrating engagement of a coronal advancer and a coronal lifter of an expandable ALIF device, particularly showing how a lifter engagement area of the coronal advancer and an advancer engagement area of the coronal lifter fit together.
Figure 11B:
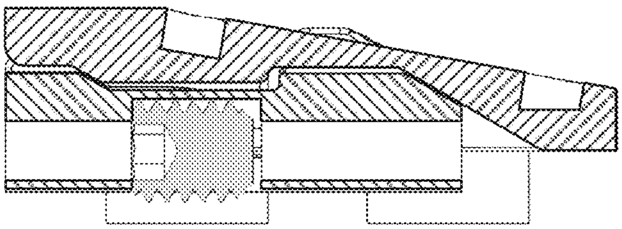
Figure 11C:
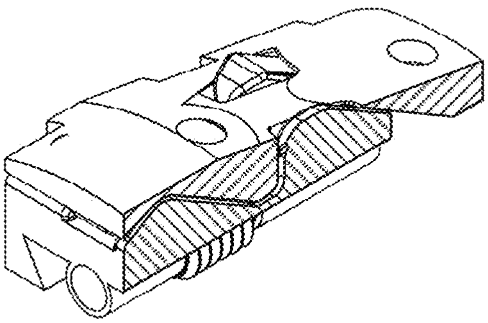
Figure 11D:
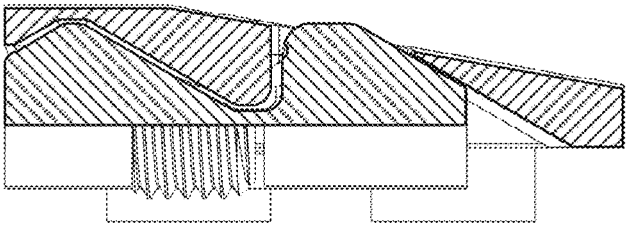
Figure 11E:
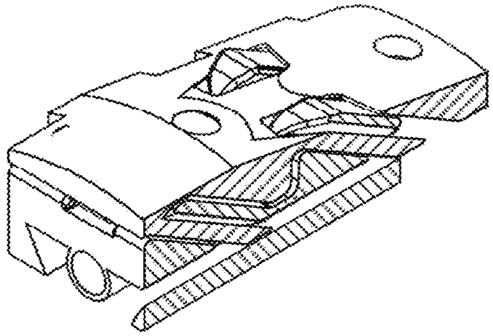
Figure 11F:
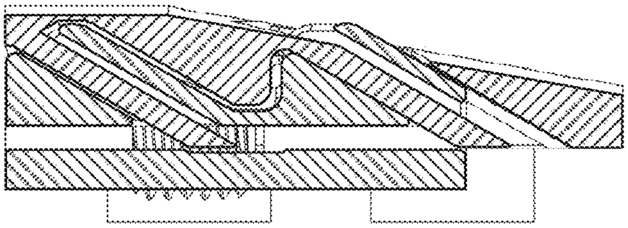
Figure 11G:
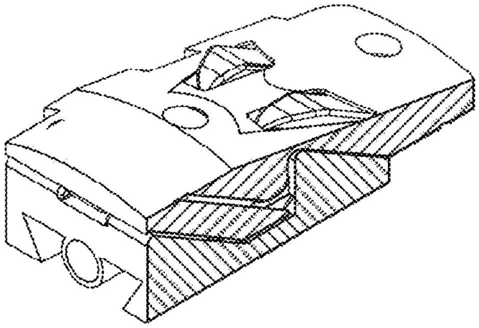
Figure 11H:
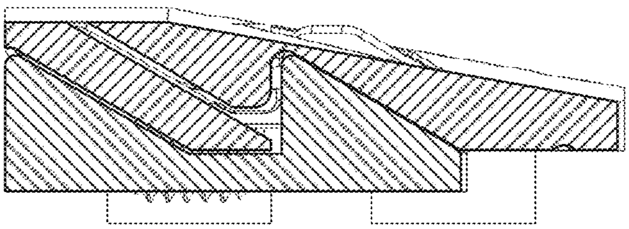

FIGS. 10A-10C show the coronal advancer 105 and the coronal lifter 106 engaged with one another. FIG. 10A shows interfacing between the substrate riser wedges 157 of the coronal advancer 105 and the ceiling lifter wedges 167 of the coronal lifter 106, and FIG. 10B shows how advancement of the coronal advancer 105 along the anteroposterior axis results in translation of the coronal lifter 106 along the craniocaudal axis. FIG. 10C shows a cutaway view of the coronal advancer 105 and the coronal lifter 106, specifically showing a dovetail engagement between the winged riser wedges 158 of the coronal advancer 105 and the winged lifter wedges 168 of the coronal lifter 106. For further clarity, FIGS. 11A-11H provide a series of sequential cutaway views demonstrating engagement between the riser wedges 156 of the coronal advancer 105 and the complementary lifter wedges 166 of the coronal lifter 106.

2.4 Sagittal Adjustment Mechanism

As discussed in Section 1.2 of the present disclosure and FIGS. 6A-6F, the sagittal adjustment mechanism of the ALIF device 100 includes the sagittal advancer 108 which engages a bottom portion of the center body 101 and serves to rotate an anterior portion of the second plate 103 around an axis defined by the plate pin 109 as the sagittal advancer 108 moves in a first direction along the anteroposterior axis. Actuation of the sagittal advancer 108 in the first direction or the second direction along the anteroposterior axis is controlled by the sagittal advancer screw 107, which is captured along a top portion of the sagittal advancer 108 and engages the center body 101 at the threaded bore element 116 of the sagittal advancer track 115. Rotation of the sagittal advancer screw 107 within the threaded bore element 116 causes translation of the sagittal advancer 108 along the sagittal advancer track 115 of the center body 101 in the first direction or the second direction along the anteroposterior axis.

Figure 12A:
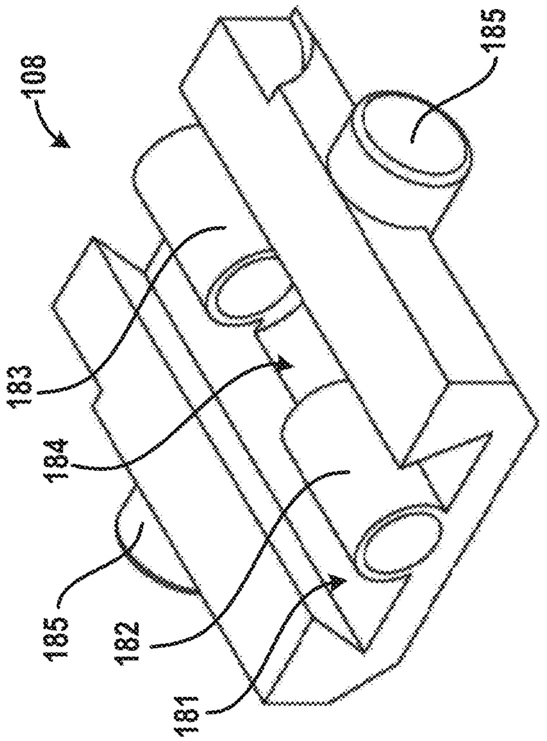
FIGS. 12A and 12B are a pair of illustrations showing a sagittal advancer for sagittal expansion of an expandable ALIF device, where
Figure 12B:
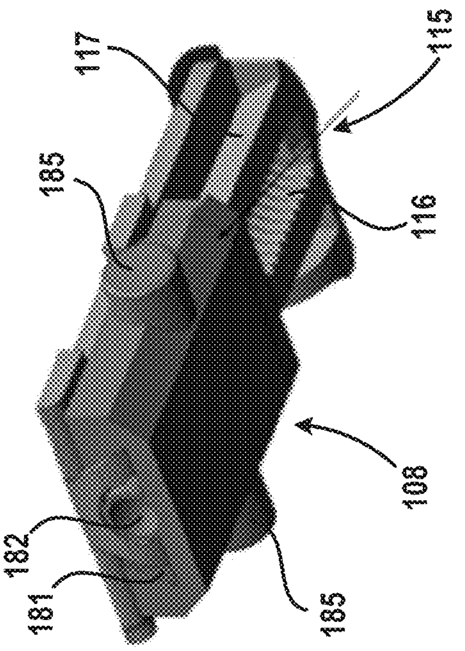

FIG. 12A shows a top perspective view of the sagittal advancer 108. A top portion of the sagittal advancer 108 includes a complementary dovetail portion 181 that engages the dovetail portion 117 of the sagittal advancer track 115, as demonstrated in FIG. 12B. Within the complementary dovetail portion 181, the sagittal advancer 108 includes a first lumen 182, a second lumen 183, and an advancer screw seat 184 defining a gap between the first lumen 182 and the second lumen 183. As previously demonstrated in FIGS. 6E and 6F, the advancer screw seat 184 receives the sagittal advancer screw 107 and secures the sagittal advancer screw 107 within the threaded bore element 116 of the sagittal advancer track 115 of the center body 101. The first lumen 182 is hollow, allowing insertion of the applicator device to engage and rotate the sagittal advancer screw 107. Rotation of the sagittal advancer screw 107 causes translation of the sagittal advancer 108 along a direction of elongation of the sagittal advancer track 115 similar to the coronal advancer 105.

Further, the sagittal advancer 108 includes one or more sliders 185 which protrude from lateral sides of the sagittal advancer 108 as shown. Each slider 185 is configured to engage a respective slider track 136 of the second plate 103 in a "pin and slot"-like engagement as shown in FIGS. 6A and 6B. Importantly, as the sagittal advancer 108 moves in the first direction along the sagittal advancer track 115 (following the anteroposterior axis), the sliders 185 each move from a first position within an associated respective slider track 136 (see FIG. 6A) to a second position within the associated respective slider track 136 (see FIG. 6B). A first portion of the slider track 136 corresponding with the first position of the slider 185 of the sagittal advancer 108 is located inferior to a second portion of the slider track 136 corresponding with the second position first position of the slider 185 of the sagittal advancer 108. Because the slider tracks 136 of the second plate 103 are angled as shown in FIGS. 6A and 6B, and because the second plate 103 is rotatably coupled to the posterior portion of the center body 101 (by the plate pin 109), this action causes the anterior portion of the second plate 103 to rotate about an axis defined by the plate pin 109 downward relative to the center body 101 and the first plate 102, thereby increasing the angle between the first plate 102 and the second plate 103.

3. Applicator Device and Fusion System

Figure 13A:
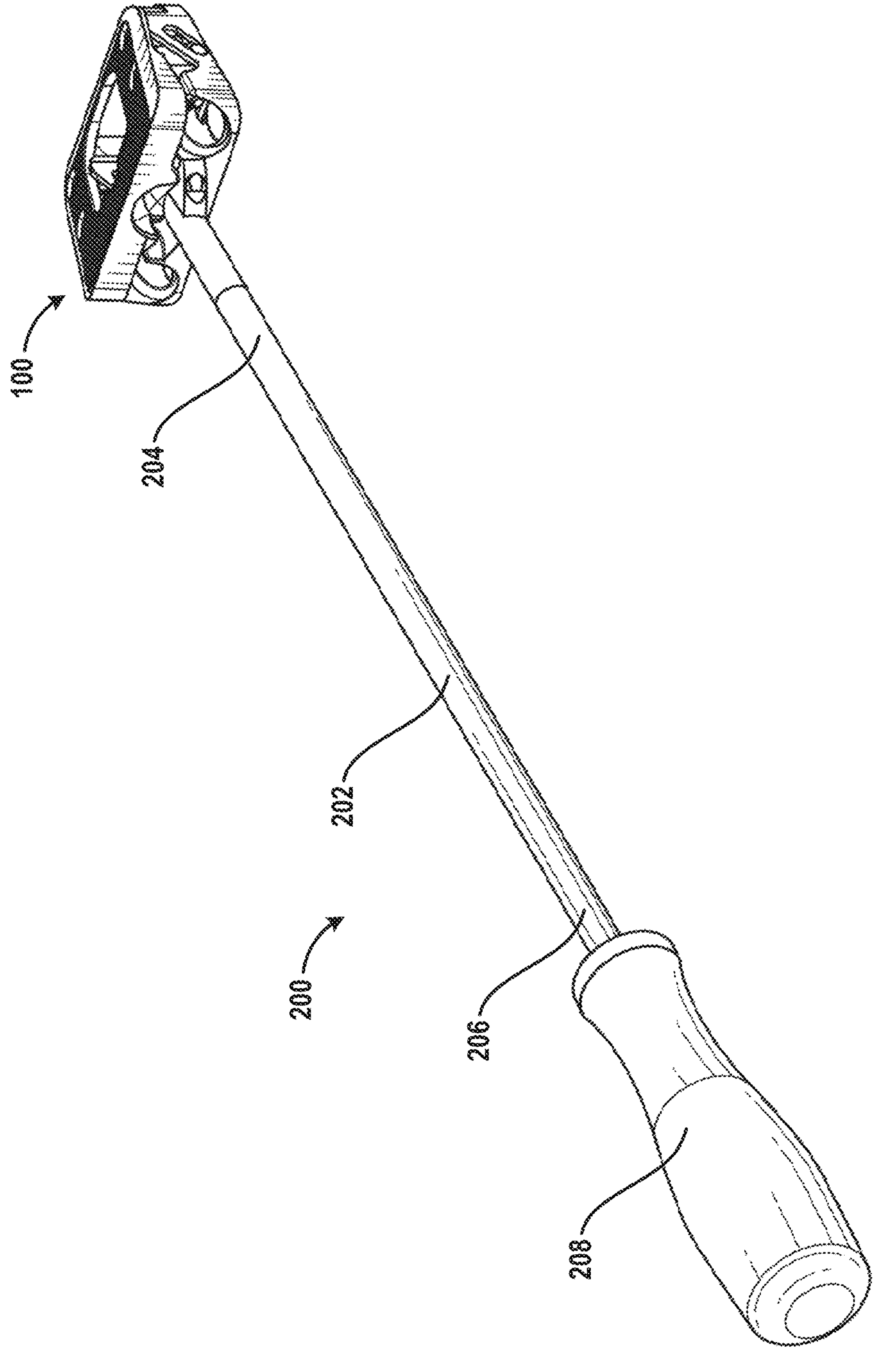
FIGS. 13A-13C are a series of illustrations showing an applicator device for insertion and adjustment of an expandable ALIF device, where
Figure 13B:
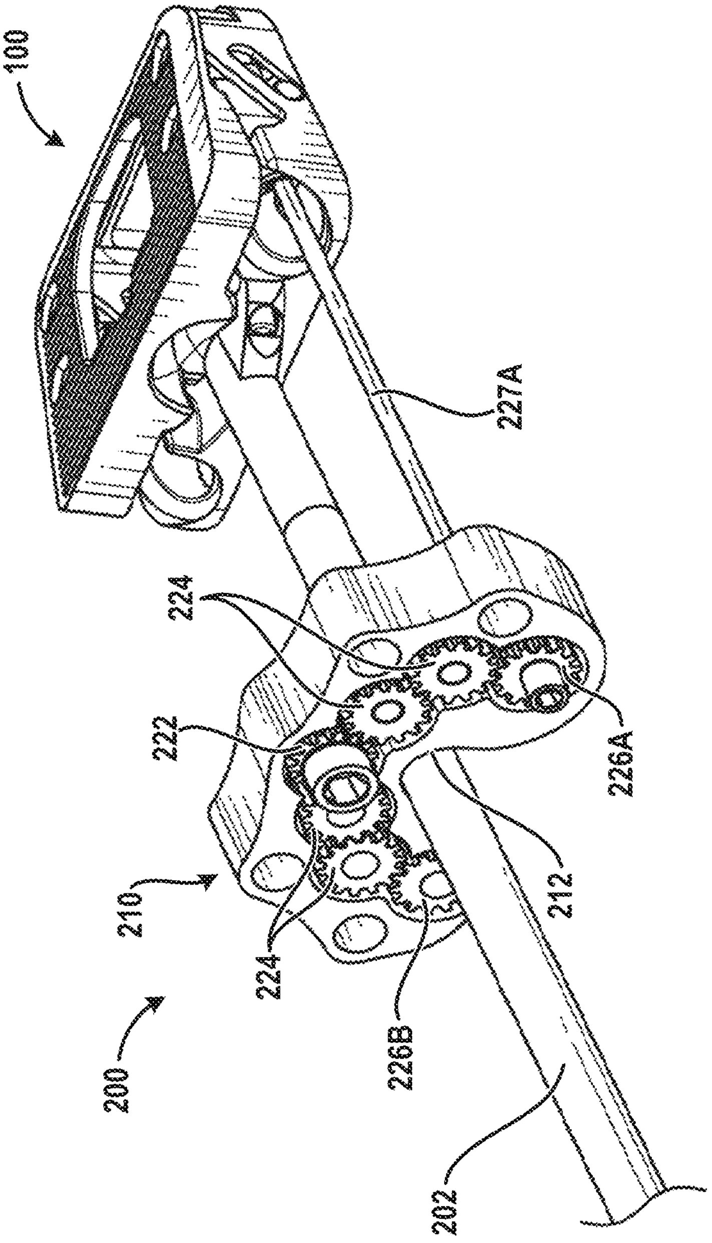
Figure 13C:
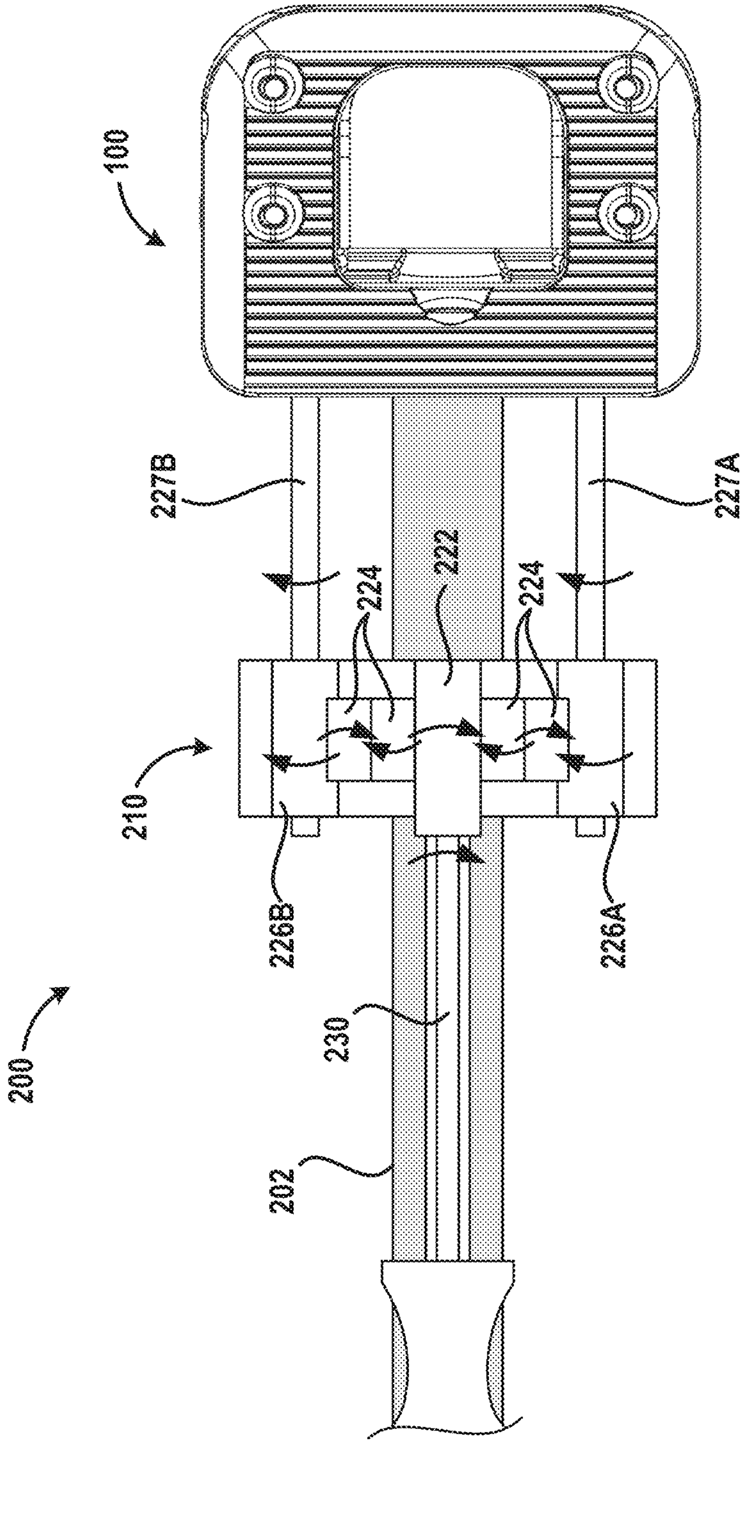

The ALIF device 100 may be adjusted as outlined above using an applicator device 200 shown in FIGS. 13A-13C. The applicator device 200 can include a member 202 having a distal portion 204 that engages the center body 101 of the ALIF device 100 through a channel collectively defined by the central access feature 110, the upper access feature 120, and the lower access feature 130. Further, the member 202 includes a proximal portion 206 defining a handle 208. The applicator device 200 is configured to engage and subsequently rotate one or more of the coronal advancer screw 104 and the sagittal advancer screw(s) 107. A gearing arrangement of the applicator device enables simultaneous rotation of both sagittal advancer screws 107 in the same direction and to the same degree. The applicator device 200 may be coupled to the ALIF device 100 to facilitate placement of the ALIF device 100 between vertebrae from an anterior approach. In some examples, the applicator device 200 must be strong enough to withstand a hammering action to place the ALIF device 100 between vertebrae. Following placement and adjustment of the ALIF device 100, the applicator device 200 can be decoupled from the ALIF device 100.

As shown, the applicator device 200 can include a gearbox 210 associated with the distal portion 204. The gearbox 210 can include a saddle portion 212 that can rest along the member 202. A gearing arrangement of the gearbox can include a primary gear 222, a plurality of intermediate gears 224, a first terminal gear 226A in operative association with a first driver member 227A, and a second terminal gear 226B in operative association with a second driver member 227B. The primary gear 222 can interface with a central driver member 230 for manual (or machine-driven) rotation. As demonstrated in FIG. 13C, rotation of the primary gear 222 by the central driver member 230 causes rotation of the plurality of intermediate gears 224, which in turn causes rotation of the first driver member 227A and the second driver member 227B by rotating the first terminal gear 226A and the second terminal gear 226B.

When the first driver member 227A and the second driver member 227B are respectively engaged with the first coronal advancer screw 104A and the second coronal advancer screw 104B (shown in FIG. 4C), rotating the primary gear 222 results in simultaneous and equal advancement of the first coronal advancer screw 104A and the second coronal advancer screw 104B (and thus the first coronal advancer 105A and the second coronal advancer 105B) along the first coronal advancer track 111A and the second coronal advancer track 111B.

Likewise, when the first driver member 227A and the second driver member 227B are respectively engaged with the first sagittal advancer screw 107A and the second sagittal advancer screw 107B (shown in FIG. 4C), rotating the primary gear 222 results in simultaneous advancement of the first sagittal advancer screw 107A and the second sagittal advancer screw 107B (and thus the first sagittal advancer 108A and the second sagittal advancer 108B) along the first sagittal advancer track 115A and the second sagittal advancer track 115B.

As shown in FIG. 13B, one of the first coronal advancer screw 104A or the second coronal advancer screw 104B could be individually adjusted using the applicator device 200 by decoupling one of the first driver member 227A or the second driver member 227B (for the opposite side than the one being adjusted) and subsequently rotating the primary gear 222.

Figure 14:
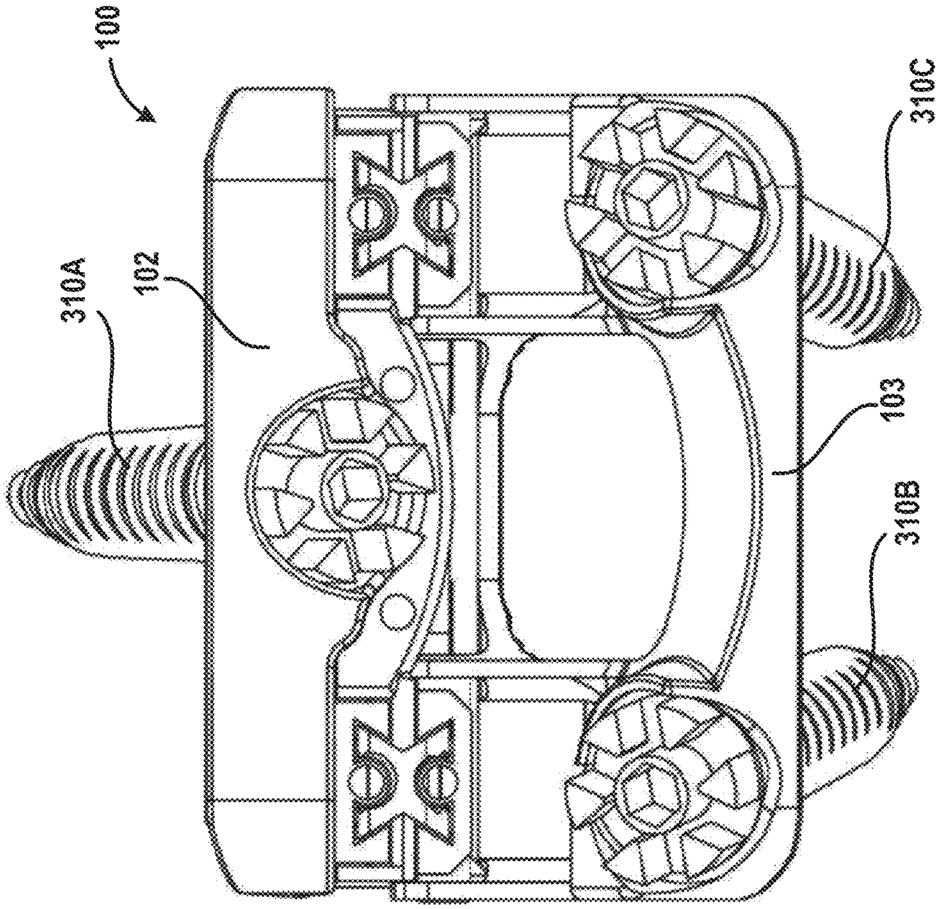
FIG. 14 is an illustration showing an expandable ALIF device having anchoring screws for securing the expandable ALIF device to bone.

FIG. 14 shows anchoring screws 310A-310C inserted into the first plate 102 and the second plate 103 for coupling the first plate 102 and the second plate 103 to respective first and second vertebrae 2 and 4 of the vertebral structure (FIGS. 1A and 1B).

Figure 15:
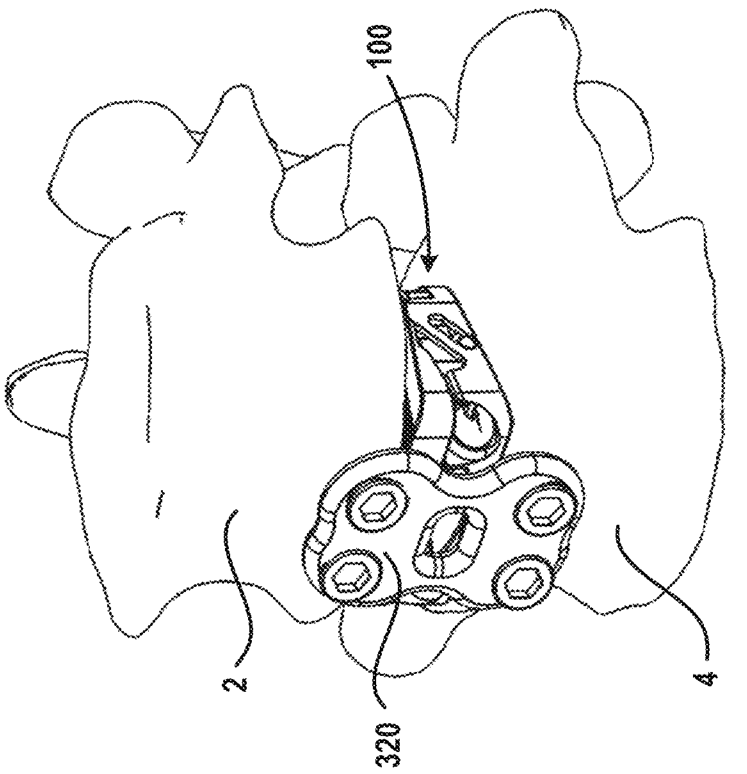
FIG. 15 is an illustration showing an anterior plate that couples along an expandable ALIF device to improve stability of the spine and aid in the correction process.

FIG. 15 shows an anterior plate 320 that can be affixed over the anterior portions of the ALIF device 100, exterior to the first plate 102 and the second plate 103 to improve stability of the spine and aid in the correction process. The anterior plate 320 can be placed over the anterior spine at the operative level. Further, anchoring screws can be positioned through screw holes of the anterior plate at a selected angle.

The ALIF device 100 and associated components (screws, the anterior plate, etc.) can be fabricated using techniques including 3-D printing, and may be made using biocompatible materials including titanium.

In some examples, the ALIF device 100 can incorporate a locking mechanism that prevents unintended coronal or sagittal adjustment.

4. Functional Operation of ALIF Device

A method of interbody fusion outlined herein includes: inserting an adjustable intervertebral device (ALIF device 100) into an intervertebral disc space, the adjustable intervertebral device including the center body 101 captured between the first plate 102 and the second plate 103.

The method can further include: adjusting a coronal alignment of the first plate 102 by engaging the coronal advancer screw 104 (optionally by the applicator device 200) and rotating the coronal advancer screw 104 within the coronal advancer track 111. This advances the coronal advancer 105 along the coronal advancer track 111 of the center body 101, where advancement of the coronal advancer 105 along the coronal advancer track 111 causes translation of the coronal lifter 106 and a lateral portion of the first plate 102 along the craniocaudal axis relative to the center body 101.

The method can further include: adjusting a sagittal alignment of the second plate 103, by engaging the sagittal advancer screw 107 (optionally by the applicator device 200) and rotating the sagittal advancer screw 107. This advances the sagittal advancer 108 along the sagittal advancer track 115 of the center body 101, where advancement of the sagittal advancer 108 along the sagittal advancer track 115 causes rotation of an anterior portion of the second plate 103 relative to the center body 101.

The functions performed in the processes and methods may be implemented in differing order. Furthermore, the outlined steps and operations are provided as examples, and some of the steps and operations may be optional, combined into fewer steps and operations, or expanded into additional steps and operations without detracting from the essence of the disclosed embodiments.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An adjustable intervertebral device, comprising:

a center body captured between a first plate and a second plate, wherein the center body defines a top surface having a coronal advancer track and a bottom surface having a sagittal advancer track, wherein the first plate includes a first lateral portion and a second lateral portion opposite the first lateral portion along a mediolateral axis, and wherein the second plate includes an anterior portion and a posterior portion opposite the anterior portion, the posterior portion of the second plate being coupled to a posterior portion of the center body such that the anterior portion of the second plate is rotatable relative to the center body about an axis that is parallel to the mediolateral axis;

a coronal adjustment mechanism, comprising: (i) a coronal advancer advanceable along the coronal advancer track by a coronal advancer screw; and (ii) a coronal lifter positioned between the coronal advancer and a bottom portion of the first lateral portion of the first plate, the coronal lifter being distinct from the first plate; wherein advancement of the coronal advancer along the coronal advancer track causes translation of the coronal lifter along a craniocaudal axis relative to the center body, and wherein translation of the coronal lifter along the craniocaudal axis causes differential translation of the first lateral portion of the first plate along the craniocaudal axis relative to the center body and the second lateral portion of the first plate; and a sagittal advancer advanceable along the sagittal advancer track by a sagittal advancer screw wherein advancement of the sagittal advancer along the sagittal advancer track causes rotation of an anterior portion of the second plate relative to the center body about the axis that is parallel to the mediolateral axis.

2. The adjustable intervertebral device of claim 1, wherein rotation of the coronal advancer screw within a threaded bore portion of the coronal advancer track causes advancement of the coronal advancer along the coronal advancer track.

3. The adjustable intervertebral device of claim 1, wherein the coronal advancer includes a riser wedge that engages a complementary riser wedge of the coronal lifter.

4. The adjustable intervertebral device of claim 1, further comprising:

an anterior plate configured to engage the center body from an anterior approach, the anterior plate being configured to receive one or more anchoring screws.

5. The adjustable intervertebral device of claim 1, wherein the coronal lifter engages a coronal lifter track of the center body that directs translation of the coronal lifter along the craniocaudal axis.

6. The adjustable intervertebral device of claim 1, wherein rotation of the sagittal advancer screw within a threaded bore portion of the sagittal advancer track causes advancement of the sagittal advancer along the sagittal advancer track.

7. The adjustable intervertebral device of claim 1, wherein advancement of the sagittal advancer causes translation of a slider of the sagittal advancer between a first position and a second position along a slider track of the second plate, and wherein translation of the slider of the sagittal advancer along the slider track of the second plate causes rotation of the second plate relative to the center body.

8. The adjustable intervertebral device of claim 7, wherein translation of the slider of the sagittal advancer from the first position to the second position along the slider track of the second plate increases an angle between the second plate and the center body.

9. The adjustable intervertebral device of claim 7, wherein translation of the slider of the sagittal advancer from the second position to the first position along the slider track of the second plate decreases an angle between the second plate and the center body.

10. The adjustable intervertebral device of claim 7, wherein a first portion of the slider track corresponding with the first position is located inferior to a second portion of the slider track corresponding with the second position.

11. The adjustable intervertebral device of claim 7, the first plate being operable to engage a lower surface of a first vertebra and the second plate being operable to engage an upper surface of a second vertebra, the second vertebra being positioned below the first vertebra.

12. A system for implanting and adjusting an adjustable intervertebral device, comprising:

an adjustable intervertebral device, including:

a center body captured between a first plate and a second plate, wherein the center body defines a top surface having a coronal advancer track and a bottom surface having a sagittal advancer track, wherein the first plate includes a first lateral portion and a second lateral portion opposite the first lateral portion along a mediolateral axis, and wherein the second plate includes an anterior portion and a posterior portion opposite the anterior portion, the posterior portion of the second plate being coupled to a posterior portion of the center body such that the anterior portion of the second plate is rotatable relative to the center body about an axis that is parallel to the mediolateral axis;

a coronal adjustment mechanism, comprising: (i) a coronal advancer advanceable along the coronal advancer track by a coronal advancer screw and (ii) a coronal lifter positioned between the coronal advancer and a bottom portion of the first lateral portion of the first plate, the coronal lifter being distinct from the first plate; wherein advancement of the coronal advancer along the coronal advancer track causes translation of the coronal lifter along a craniocaudal axis relative to the center body, and wherein translation of the coronal lifter along the craniocaudal axis causes differential translation of the first lateral portion of the first plate along the craniocaudal axis relative to the center body and the second lateral portion of the first plate; and a sagittal advancer advanceable along the sagittal advancer track by a sagittal advancer screw, wherein advancement of the sagittal advancer along the sagittal advancer track causes rotation of the anterior portion of the second plate relative to the center body about the axis that is parallel to the mediolateral axis; and an applicator configured to engage and subsequently rotate one or more of the coronal advancer screw and the sagittal advancer screw.

13. The system of claim 12, further comprising one or more anchoring screws, wherein the adjustable intervertebral device is operable to receive the one or more anchoring screws to couple the adjustable intervertebral device to a vertebral structure.

14. The system of claim 12, wherein rotation of the coronal advancer screw within a threaded bore portion of the coronal advancer track causes advancement of the coronal advancer along the coronal advancer track.

15. The system of claim 12, wherein rotation of the sagittal advancer screw within a threaded bore portion of the sagittal advancer track causes advancement of the sagittal advancer along the sagittal advancer track.

16. A method of interbody fusion, comprising:

inserting an adjustable intervertebral device into an intervertebral disc space, the adjustable intervertebral device including a center body captured between a first plate and a second plate, wherein the center body defines a top surface having a coronal advancer track and a bottom surface having a sagittal advancer track, wherein the first plate includes a first lateral portion and a second lateral portion opposite the first lateral portion along a mediolateral axis, and wherein the second plate includes an anterior portion and a posterior portion opposite the anterior portion, the posterior portion of the second plate being coupled to a posterior portion of the center body such that the anterior portion of the second plate is rotatable relative to the center body about an axis that is parallel to the mediolateral axis;

adjusting a coronal alignment of the first plate using a coronal adjustment mechanism of the adjustable intervertebral device, the coronal adjustment mechanism comprising: (i) a coronal advancer advanceable along the coronal advancer track by a coronal advancer screw; and (ii) a coronal lifter positioned between the coronal advancer and a bottom portion of the first lateral portion of the first plate, the coronal lifter being distinct from the first plate; wherein advancement of the coronal advancer along the coronal advancer track causes translation of the coronal lifter along a craniocaudal axis relative to the center body, and wherein translation of the coronal lifter along the craniocaudal axis causes differential translation of the first lateral portion of the first plate along the craniocaudal axis relative to the center body and the second lateral portion of the first plate; and adjusting a sagittal alignment of the second plate using a sagittal advancer of the adjustable intervertebral device, the sagittal advancer being advanceable along the sagittal advancer track by a sagittal advancer screw, wherein advancement of the sagittal advancer along the sagittal advancer track causes rotation of the anterior portion of the second plate relative to the center body about the axis that is parallel to the mediolateral axis.

17. The method of claim 16, further comprising:

engaging the coronal advancer screw by an applicator device; and rotating the coronal advancer screw by the applicator device.

18. The method of claim 16, further comprising:

engaging the sagittal advancer screw by an applicator device; and rotating the sagittal advancer screw by the applicator device.

* * * * *